United States Patent
Kurosaki et al.

(10) Patent No.: US 11,135,409 B2
(45) Date of Patent: Oct. 5, 2021

(54) BALLOON WRAPPING APPARATUS AND BALLOON WRAPPING METHOD

(71) Applicant: TERUMO KABUSHIKI KAISHA, Tokyo (JP)

(72) Inventors: Yasuo Kurosaki, Kanagawa (JP); Hiroshi Goto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 100 days.

(21) Appl. No.: 16/288,538

(22) Filed: Feb. 28, 2019

(65) Prior Publication Data

US 2019/0192833 A1 Jun. 27, 2019

Related U.S. Application Data

(63) Continuation of application No. PCT/JP2017/034208, filed on Sep. 22, 2017.

(30) Foreign Application Priority Data

Sep. 23, 2016 (JP) ............................. JP2016-185601

(51) Int. Cl.
*B29C 53/08* (2006.01)
*A61M 25/10* (2013.01)
(Continued)

(52) U.S. Cl.
CPC ........ *A61M 25/1038* (2013.01); *A61M 25/10* (2013.01); *A61M 25/1029* (2013.01);
(Continued)

(58) Field of Classification Search
CPC ........... B23P 19/04; A61M 2025/1004; A61M 25/1027; A61M 25/1038; A61M 25/1029;
(Continued)

(56) References Cited

U.S. PATENT DOCUMENTS 5,350,361 A * 9/1994 Tsukashima ...... A61M 25/1002
264/523
7,618,252 B1 * 11/2009 Goff .................. A61M 25/1038
29/237
(Continued)

FOREIGN PATENT DOCUMENTS

CN 204379958 U 6/2015
CN 103660264 B 12/2015
(Continued)

OTHER PUBLICATIONS

English translation of JP2006271678 (Year: 2006).*
(Continued)

*Primary Examiner* — Jun S Yoo
(74) *Attorney, Agent, or Firm* — Buchanan Ingersoll & Rooney PC

(57) ABSTRACT

A balloon wrapping apparatus for folding a balloon at a distal portion of an elongated shaft includes: a pleating section that forms the balloon with pleats; a folding section that folds the pleats formed in the balloon, along a circumferential direction; and a support base that supports the shaft and can be moved toward and away from the pleating section. The pleating section includes an insertion hole through which the balloon can be inserted, and a back surface hole provided in a back surface on the side opposite to the side on which the insertion hole is provided. The pleating section includes an assisting shaft which can be inserted into the back surface hole from the rear surface side, and an interlock portion interlocking the assisting shaft with the support base. The assisting shaft is formed with a cavity portion.

19 Claims, 12 Drawing Sheets

(51) Int. Cl.
*B29C 33/76* (2006.01)
*B23P 19/04* (2006.01)

(52) U.S. Cl.
CPC .............. *B23P 19/04* (2013.01); *B29C 33/76* (2013.01); *A61M 2025/1031* (2013.01)

(58) Field of Classification Search
CPC ... B29C 53/564; B29C 53/566; B29C 53/825; B29C 53/10
See application file for complete search history.

(56) References Cited

U.S. PATENT DOCUMENTS

| | | | |
|---|---|---|---|
| 2002/0163104 A1* | 11/2002 | Motsenbocker .. | A61M 25/1002 264/320 |
| 2014/0319750 A1* | 10/2014 | Yanes ................ | A61M 25/1038 269/86 |
| 2016/0296969 A1 | 10/2016 | Kurosaki et al. | |
| 2018/0207855 A1 | 7/2018 | Kurosaki et al. | |

FOREIGN PATENT DOCUMENTS

| | | | | |
|---|---|---|---|---|
| CN | 108025163 | A | | 5/2018 |
| EP | 0 935 973 | A2 | | 8/1999 |
| EP | 3 064 247 | A1 | | 9/2016 |
| JP | 2004525704 | A | | 8/2004 |
| JP | 2006271678 | A | * | 10/2006 ........ A61M 25/1038 |
| JP | 2006271678 | A | | 10/2006 |
| WO | 2014179505 | A1 | | 11/2014 |
| WO | 2015/093585 | A1 | | 6/2015 |
| WO | 2017051877 | A1 | | 3/2017 |
| WO | 2017051878 | A1 | | 3/2017 |
| WO | 2017051879 | A1 | | 3/2017 |

OTHER PUBLICATIONS

An English Translation of the International Search Report (Form PCT/ISA/210) and the Written Opinion of the International Searching Authority (Form PCT/ISA/237) dated Dec. 19, 2017, by the Japanese Patent Office in corresponding International Application No. PCT/JP2017/034208. (6 pages).

International Search Report (PCT/ISA/210) dated Dec. 19, 2017, by the Japanese Patent Office as the International Searching Authority for International Application No. PCT/JP2017/034208.

The extended European Search Report dated Jan. 24, 2020, by the European Patent Office in corresponding European Patent Application No. 17853157.0-1132. (8 pages).

Office Action (the first Office Action) dated Nov. 4, 2020, by the State Intellectual Property Office of People's Republic of China in corresponding Chinese Patent Application No. 201780058574.6 and an English Translation of the Office Action. (13 pages).

Office Action (Notice of Reasons for Refusal) dated Mar. 29, 2021, by the Japanese Patent Office in corresponding Japanese Patent Application No. 2018-540310 and an English Translation of the Office Action. (7 pages).

\* cited by examiner

BALLOON WRAPPING APPARATUS AND BALLOON WRAPPING METHOD

CROSS-REFERENCES TO RELATED APPLICATIONS

This application is a continuation of International Application No. PCT/JP2017/034208 filed on Sep. 22, 2017, which claims priority to Japanese Application No. 2016-185601 filed on Sep. 23, 2016, the entire content of both of which is incorporated herein by reference.

FIELD OF THE INVENTION

The present invention generally relates to a balloon wrapping apparatus for wrapping a balloon of a balloon catheter and a balloon wrapping method.

BACKGROUND ART

Treatment of a lesion of a blood vessel by use of a catheter has been widely practiced because of little surgical invasiveness. For example, in percutaneous coronary angioplasty (Percutaneous Transluminal Coronary Angioplasty), a balloon catheter is used for improving blood flow by pushing open a lesion part of a coronary artery. In general, a balloon catheter includes an elongated hollow shaft, a balloon provided on the distal side of the shaft, and a hub provided on the proximal side of the shaft. The balloon catheter may be provided with a drug eluting balloon having an outer surface coated with a drug.

The balloon of a balloon catheter is required to be as small as possible in diameter when deflated, for good passing properties in a blood vessel. The balloon is formed in a small diameter form by being wrapped at the time of manufacturing the catheter. The wrapping of the balloon is conducted by a pleating step of bending the balloon to form a plurality of pleats, for example, three or four pleats in the circumferential direction, and a folding step of folding the thus formed pleats toward one side in the circumferential direction.

An example of a conventional balloon wrapping apparatus is the one described in Japanese Application Publication No. 2004-525704. The disclosed balloon wrapping apparatus has a pleating section for performing pleating, and a folding section for performing folding. In addition, the balloon wrapping apparatus has a support base which supports the shaft of the balloon catheter and which is slidable such that the balloon can be inserted into each section.

The pleating section has a plurality of blades in the circumferential direction for shaping the balloon to have the pleats. Between the plurality of blades, a space part extending along an insertion direction of the balloon is formed. In addition, the blades can be moved rotationally in such a manner as to change the shape of the space part. The balloon is inserted into the space part between the blades, and the balloon is narrowed by the blades moved rotationally, whereby pleats are formed.

The folding section has a plurality of blades movable rotationally, and the pleats formed in the balloon can be folded in the manner of winding the pleats along the circumferential direction. The balloon is inserted into a region surrounded by the plurality of blades, and the blades are moved rotationally such as to close the region between the blades, whereby the pleats formed in the balloon are folded along the circumferential direction.

When wrapping the balloon, the balloon catheter is placed on the support base, and the support base is slid toward the pleating section, whereby the balloon is advanced into the pleating section, and pleating is conducted. When the balloon is drawn out of the pleating section, the balloon is subsequently advanced into the folding section, and folding is conducted.

SUMMARY OF INVENTION

For improving passing properties of the balloon, the pleats should be formed into an accurate shape on the basis of a predetermined interval along the circumferential direction in wrapping of the balloon. For this purpose, the balloon should be positioned accurately at a center position of the pleating section. If the position of the balloon is deviated from the center position of the pleating section, the pleats formed in pleating may not become uniform. In addition, if the position of the balloon is deviated from the center position of the folding section, back folding may occur in which the pleat is folded in the reverse direction in the circumferential direction.

When the catheter is placed on the support base and the balloon is inserted into the pleating section, a portion near the distal end of the catheter having the balloon is not supported by the support base, and, therefore, the catheter is bent downward due to balloon's own weight. Accordingly, it is difficult to accurately position the balloon at the center position of the pleating section or the folding section.

The balloon wrapping apparatus disclosed here allows a balloon to be accurately positioned for insertion in relation to a pleating section and to a folding section.

According to one aspect, a balloon wrapping apparatus for wrapping a balloon provided at a distal portion of an elongated shaft of a balloon catheter comprises a pleating section configured to form the balloon with a plurality of circumferentially spaced apart pleats, and a folding section that folds the plurality of pleats formed in the balloon along a circumferential direction. A support base supports the shaft of the balloon catheter, and is movable toward and away from at least one of the pleating section and the folding section (i.e., the support base is movable toward and away from the pleating section or the folding section or both the pleating section and the folding section). The movement of the support base toward the at least one of the pleating section and the folding section while the support base supports the shaft of the balloon catheter resulting in the balloon at the distal portion of the shaft of the balloon catheter being positioned for insertion into the at least one of the pleating section and the folding section. The at least one of the pleating section and the folding section includes one side provided with an insertion hole through which the balloon is insertable during the movement of the support base toward the at least one of the pleating section and the folding section, with the at least one of the pleating section and the folding section including an other side opposite the one side and provided with a back surface hole that communicates with the insertion hole. The at least one of the pleating section and the folding section including an assisting shaft positioned to be inserted into the back surface hole from a back surface side of the other side, with the at least one of the pleating section and the folding section also including an interlock portion configured to interlock with a part of the assisting shaft that is not inserted into the back surface hole while the assisting shaft is inserted into the back surface hole. The assisting shaft includes a cavity portion from a side facing the back surface hole.

In the balloon wrapping apparatus configured as above, the assisting shaft can be inserted into the back surface hole and caused to reach the insertion hole, and the shaft of the balloon catheter or the core metal member inserted in the shaft can be inserted into and held in the cavity portion of the assisting shaft. Further, since the assisting shaft is moved together with the support base by interlocking the assisting shaft with the support base by the interlock portion, the balloon can be inserted into the insertion hole while maintaining the state in which the balloon is held by the assisting shaft. By this, the distal portion of the shaft is supported by the assisting shaft such as not to bend, and, therefore, the balloon can be accurately positioned in relation to and inserted into the pleating section and the folding section. For this reason, the pleats of the balloon can be formed uniformly in the circumferential direction at the pleating section, and generation of back folding can be restrained when the pleats are folded at the folding section.

The balloon wrapping apparatus may further include a metal core member to be inserted in and passed through the shaft, and the core metal may be insertable into the cavity portion of the assisting shaft. This configuration ensures that by the combination of the assisting shaft and the core metal member, the distal portion of the shaft can be supported such as not to bend, in a more assured manner. Therefore, the balloon can be accurately positioned in relation to and inserted into the pleating section and the folding section.

At least one of the pleating section and the folding section may include a plurality of blades aligned in the circumferential direction for giving a shape to the balloon, and two films passing through a central portion surrounded by the plurality of blades, and the assisting shaft may have the decreasing diameter portion decreasing in outside diameter toward the back surface hole. This permits the decreasing diameter portion of the assisting shaft to smoothly pass between the two films.

The blades may extend in the direction from the insertion hole toward the back surface hole, and the direction in which the assisting shaft can be moved together with the support base may be parallel to the extending direction of the blades. This permits the balloon supported by the assisting shaft to be accurately positioned at a central portion of the blades. With the balloon accurately positioned at the central portion of the blades, the pleats can be formed uniformly in the circumferential direction at the pleating section, and generation of back folding can be restrained when the pleats are folded at the folding section.

The assisting shaft may include an elongated shaft main body, and an inner surface member which is disposed on the shaft main body, is formed with the cavity portion, and is formed of a material higher in frictional coefficient than the shaft main body. This makes it possible to restrain the shaft or the core metal member of the balloon catheter inserted in the cavity portion from slipping, and to favorably hold them on the assisting shaft.

The assisting shaft may include an elongated shaft main body, and an inner surface member which is disposed on the shaft main body, is formed with the cavity portion, and is formed of an elastic material. This permits the shaft or the core metal member of the balloon catheter inserted in the cavity portion to be favorably held by being clamped by the inner surface member which is elastically deformed.

The cavity portion of the assisting shaft may decrease in inside diameter toward the depth side. This permits the shaft or the core metal member of the balloon catheter to be favorably held by being clamped by the cavity portion.

A maximum diameter of the assisting shaft may be greater than the diameter of the balloon. This makes it possible to restrain the balloon from making contact with other member when the balloon held by the assisting shaft is moved in the axial direction together with the assisting shaft.

At least one of the pleating section and the folding section may have a plurality of blades aligned in the circumferential direction for giving a shape to the balloon, and the core metal member may be longer than the length in the extending direction of the blades by not less than 10 mm. This permits the metal core member to be placed on both the assisting shaft and the support base, and permits the shaft of the balloon catheter to be securely supported and restrained from bending.

Another aspect of the disclosure here involves a balloon wrapping apparatus for wrapping a balloon at a distal portion of an elongated shaft of a balloon catheter, wherein the distal portion of the elongated shaft terminates in a free end. The balloon wrapping apparatus comprises: a pleating section, a folding section and a support base. The pleating section is comprised of first and second walls spaced apart from one another so that a space exists in the pleating section between the first and second walls into which is movable the balloon at the distal portion of the elongated shaft of the balloon catheter. The space in the pleating section contains a first plurality of rotatable blades that engage the balloon when the balloon is positioned in the space to form a plurality of circumferentially spaced apart pleats on the balloon. The folding section is comprised of first and second walls spaced apart from one another so that a space exists between the first and second walls of the folding section into which is movable the balloon at the distal portion of the elongated shaft of the balloon catheter, with the space in the folding section containing a second plurality of rotatable blades that engage the balloon when the balloon is positioned in the space in the folding section to fold the pleats along a circumferential direction. The first and second walls of one of the pleating section and the folding section (i.e., the first and second walls of the pleating section or the folding section or both the pleating section and the folding section) including a first through hole and a second through hole respectively, with the first and second through holes aligned with one another. The support base is configured to support the shaft of the balloon catheter. The support base is movable in a first direction toward the first wall of the one of the pleating section and the folding section so that the balloon on the distal portion of the shaft approaches the first through hole. The one of the pleating section and the folding section includes an elongated assisting shaft projecting toward the second wall of the one of the pleating section and the folding section. The assisting shaft is movable in a second direction, opposite the first direction, toward the second wall to cause the assisting shaft to pass through the second through hole and to interact with the shaft of the balloon catheter supported on the support base so that the assisting shaft supports the free end of the shaft to prevent the shaft from bending due to gravity.

Another aspect of the disclosure here involves a balloon wrapping method for wrapping a balloon provided at a distal portion of an elongated shaft of a balloon catheter. The balloon wrapping method comprises: performing first and second operations on the balloon provided at the distal portion of the elongated shaft of the balloon catheter, with one of the first and second operations being a pleat forming operation in which pleats are formed on the balloon, and the other of the first and second operations being a pleat wrapping operation in which the pleats are folded along a circumferential direction of the elongated shaft. The first operation comprises: mounting the shaft of the balloon catheter on a support base, wherein the shaft of the balloon catheter on the support base possessing a free end at the distal portion of the shaft; moving the shaft of the balloon catheter toward an outer surface of a first wall provided with a first through hole, with the first wall possessing an inner surface opposite the outer surface and facing an inner surface of a second wall, and the inner surface of the first wall being spaced from the inner surface of the second wall so that a space exists between the first and second walls, and the first wall including a first through hole and the second wall including a second through hole; moving an assisting shaft toward an outer surface of the second wall that is opposite the inner surface of the second wall; moving the assisting shaft through the second through hole; moving the shaft of the balloon catheter through the first through hole to position the balloon in the space between the first and second walls; and supporting the free end of the shaft by way of the assisting shaft while the balloon is positioned in the space to prevent the shaft from bending due to gravity. The first operation is performed while the balloon is positioned in the space and while the free end of the shaft is supported by way of the assisting shaft.

BRIEF DESCRIPTION OF DRAWINGS

FIGS. 10(A)-10(E) depict side views explaining a pleat forming operation and an operation of the assisting shaft provided in the pleating section, wherein FIG. 10(A) depicts a state before the balloon catheter is supported by the assisting shaft, FIG. 10(B) depicts a state in which the balloon catheter is supported by the assisting shaft, FIG. 10(C) depicts a state in which insertion of the balloon catheter is assisted by the assisting shaft, FIG. 10(D) depicts a state in which the balloon catheter has been drawn out of the pleating section, and FIG. 10(E) depicts a state in which the assisting shaft has been drawn out of the pleating section.

FIG. 17(B) depicts a state in which the balloon catheter is supported by the assisting shaft, FIG. 17(C) depicts a state in which insertion of the balloon catheter is assisted by the assisting shaft, FIG. 17(D) depicts a state in which the balloon catheter has been drawn out of the folding section, and FIG. 17(E) denotes a state in which the assisting shaft has been drawn out of the folding section.

MODES FOR CARRYING OUT THE INVENTION

Set forth below with reference to the accompanying drawings is a detailed description of an embodiment of a balloon wrapping apparatus and balloon wrapping method representing examples of the inventive balloon wrapping apparatus and balloon wrapping method disclosed here. The dimensions or scales on the drawings may be exaggerated or different from actuality/reality for convenience of description and illustration. In the description below, the side of insertion of a balloon catheter 10 into a body lumen will be referred to as "distal end" or "distal side," and the side of an operator's hand operation will be referred to as "proximal end" or "proximal side."

A balloon wrapping apparatus according to the present embodiment is an apparatus capable of wrapping or is configured to wrap a balloon 52 (i.e., the balloon wrapping apparatus wraps a balloon) so as to wrap the balloon 52 around a shaft 51, at the time of manufacturing a balloon catheter 50 having a balloon 52 at a distal portion of an elongated shaft 51.

The balloon catheter to be wrapped may be subjected to hydrophilic coating for the purpose of improving properties for delivery to a lesion part, or may have a balloon surface subjected to a surface treatment such as a plasma treatment or irradiation with UV rays, but this is not particularly restrictive. There can also be used a balloon catheter in which the surface of a balloon has been subjected to a drug coating for delivery of a drug to a lesion part.

Figure 1:
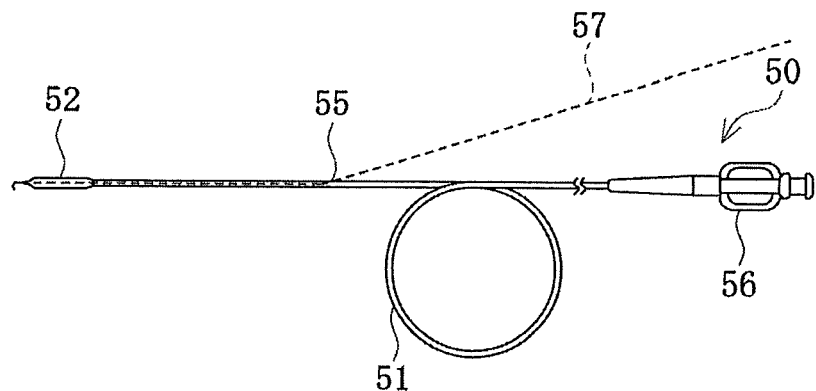
FIG. 1 is a front view of a rapid exchange type balloon catheter.

In the first place, a balloon catheter 50 will be described. As depicted in FIG. 1, the balloon catheter 50 includes an elongated hollow shaft 51, a balloon 52 provided at a distal-side end portion of the shaft 51, and a hub 56 secured to a proximal-side end portion of the shaft 51.

Where this balloon catheter 50 is used in such a manner that the elongated shaft 51 is inserted into and passed through a body organ and the balloon 52 provided on the distal side of the elongated shaft 51 is inflated at a lesion part, it is thereby possible to push open the lesion part and to perform a treatment. The shaft 51 is provided, at a position near the distal side, with an opening 55 through which to introduce a guide wire. In other words, this balloon catheter 50 is a so-called rapid exchange type catheter.

Figure 2:
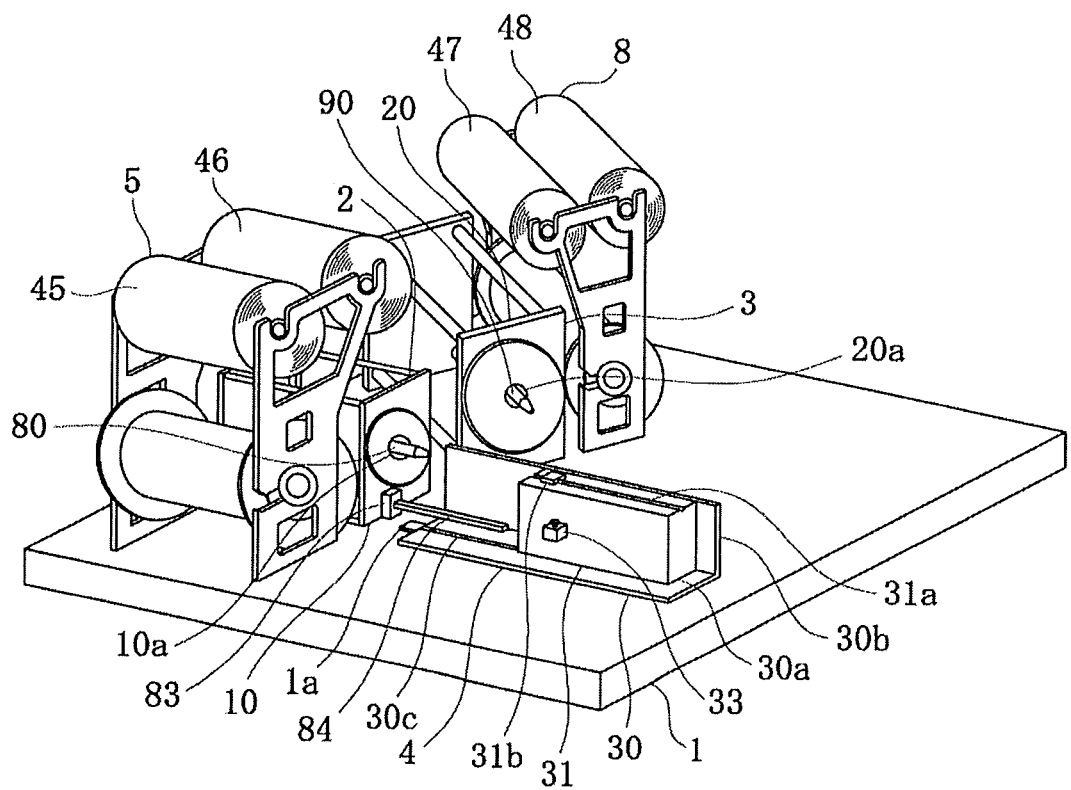
FIG. 2 is a perspective view of a balloon wrapping apparatus.

The balloon wrapping apparatus will now be described. As depicted in FIG. 2, the balloon wrapping apparatus has a pleating section 2 and a folding section 3 and a support base 4 disposed on a base 1 formed in a base shape. The pleating section 2 is capable of forming or is configured to form the balloon 52 with pleats (i.e., the pleating section forms the balloon 52 with pleats). The folding section 3 is capable of folding or is configured to fold the pleats (i.e., the folding section 3 folds the wind shapes) formed in the balloon 52 in the manner of winding the pleats around an inner tube 54 of the shaft 51. The balloon catheter 50 can be placed and held on the support base 4. The pleats formed in the balloon 52 are formed of pleats of balloon thin film material having a length extending substantially in a major axis direction of the balloon 52, and are so formed that the pleats project in the circumferential direction from the major axis of the balloon 52, as viewed in a section perpendicular to the major axis of the balloon 52. The length of the pleats in the major axis direction does not exceed the length of the balloon 52, and is approximately 3 to 400 mm, preferably approximately 3 to 300 mm, more preferably approximately 30 to 300 mm, and further preferably approximately 40 to 200 mm. The length by which the pleat projects in the circumferential direction from the shaft 51 is 1 to 8 mm. The number of the pleats is not particularly limited, and can be selected from among two, three, four, five, six and seven. In the present embodiment, the number of the pleats is three.

The length of the balloon 52 in a major axis direction is not particularly limited, and is greater than approximately 3 mm. Preferably, the length of the balloon in the major axis direction is approximately 20 to 400 mm, more preferably 30 to 300 mm, and further preferably approximately 40 to 200 mm. The diameter of the balloon 52 in a minor axis direction (the direction orthogonal to the major axis direction) is not particularly restricted, and is preferably not less than 1 mm, more preferably 1 to 10 mm, still more preferably 2 to 8 mm, and further preferably 2 to 4 mm. The material of the balloon 52 is not specifically restricted so long as it is flexible, and is composed, for example, of one or more of polyamides and polyamide elastomers. The surface of the balloon 52 preferably has a smooth surface, but it may not necessarily be smooth. The surface of the balloon 52 may have minute pores that do not penetrate the film, but may not necessarily have minute pores.

A film supplying section 5 for supplying a first film 45 and a second film 46 to the pleating section 2 is disposed on the base 1, adjacent to the pleating section 2. In addition, a film supplying section 8 is disposed on the base 1, adjacent to the folding section 3, whereby a first film 47 and a second film 48 can be supplied. The first film 47 and the second film 48 are independent separate films, but the same series of films may also be used. That is, the first film 47 and the second film 48 can be constituted by the same or a common film.

Figure 4:
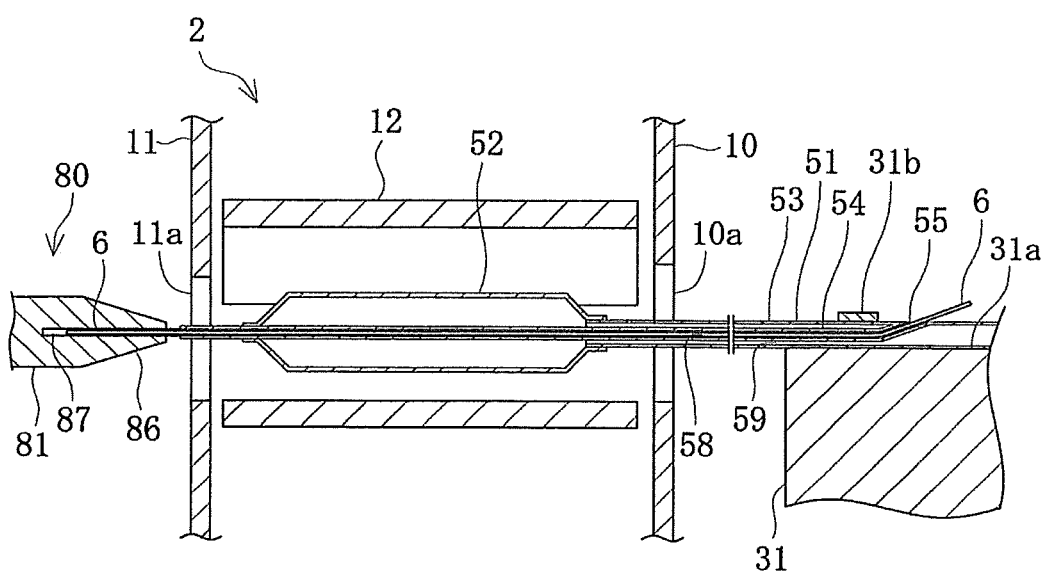
FIG. 4 is a cross-sectional view of the balloon catheter and the pleating section in a state in which a balloon is inserted in the pleating section.

The pleating section 2 has a front surface plate or wall 10 and a back surface plate or wall 11 (see FIG. 4) perpendicular to the base 1. As shown in FIG. 4, the front surface plate 10 and the back surface plate 11 are spaced apart from one another so that a space exists between the two plates or walls 10, 11. The front surface plate 10 has an insertion hole 10a through which a distal portion of the balloon catheter 50 can be inserted. The back surface plate 11 has a back surface hole 11a (see FIG. 4) communicating with and aligned with the insertion hole 10a. The pleating section 2 is provided with a first insertion assisting section 80 that assists insertion of the balloon catheter 50 into the insertion hole 10a.

Figure 12:
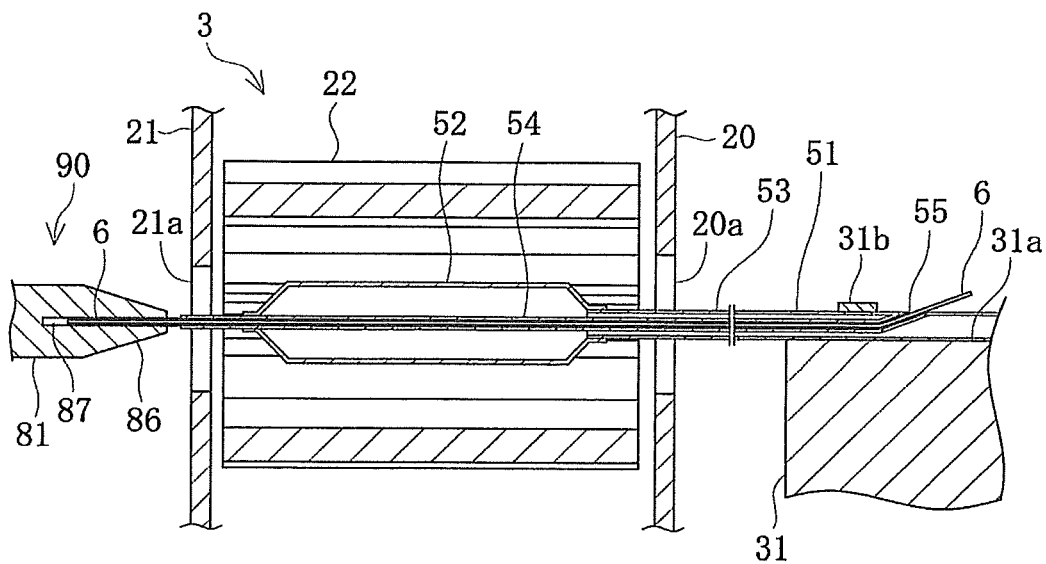
FIG. 12 is a cross-sectional view of the balloon catheter and the folding section in a state in which the balloon is inserted in the folding section.

In addition, the folding section 3 has a front surface plate or wall 20 and a back surface plate or wall 21 (see FIG. 12) perpendicular to the base 1. As shown in FIG. 12, the front surface plate 20 and the back surface plate 21 are spaced apart from one another so that a space exists between the two plates or walls 20, 21. The front surface plate 20 has an insertion hole 20a through which the distal portion of the balloon catheter 50 can be inserted. The front surface plate 20 of the folding section 3 is oriented in a direction different by a predetermined angle from a direction in which the front surface plate 10 of the pleating section 2 is oriented. That is, the front surface plate 20 of the folding section 3 and the front surface plate 10 of the pleating section 2 are not parallel. The back surface plate 11 has a back surface hole 21a (see FIG. 12) communicating with and aligned with the insertion hole 20a. The folding section 3 is provided with a second insertion assisting section 90 that assists insertion of the balloon catheter 50 into the insertion hole 20a.

A positioning section 1a capable of positioning the support base 4 to be oriented in two different directions is provided on the base 1. In FIG. 2, the support base 4 is positioned by the positioning section 1a in such a manner as to face the front surface plate 10 of the pleating section 2. By the positioning section 1a, the support base 4 can also be positioned in such a manner as to face the front surface plate 20 of the folding section 3.

The support base 4 includes a base section 30 placed or positioned on the base 1, and a holding base section 31 which can be moved horizontally on the base section 30. The base section 30 includes a bottom surface portion 30a placed or positioned on an upper surface of the base 1 and positioned by the positioning section 1a, and a side surface portion 30b extending vertically upward from a side portion of the bottom surface portion 30a. A slide guide portion 30c for guiding the holding base section 31 is formed at an upper surface of the bottom surface portion 30a.

The holding base section 31 is formed substantially in the shape of a rectangular parallelepiped which makes contact with the bottom surface portion 30a and the side surface portion 30b of the base section 30. A lower surface of the holding base section 31 is slidably guided by the slide guide portion 30c of the bottom surface portion 30a. An upper surface of the holding base section 31 has a groove-shaped placing portion 31a on which the shaft 51 of the balloon catheter 50 can be placed. The holding base section 31 is provided with a holding portion 31b to cover from above a part of the placing portion 31a. The holding portion 31b is capable of holding (is configured to hold), and thereby fixing (fix), the shaft 51 of the balloon catheter 50 placed on the placing portion 31a. That is, the holding portion 31b holds and fixes the balloon catheter shaft 51 positioned on the placing portion 31a.

In a state in which the support base 4 faces the front surface plate 10 of the pleating section 2, the center of the insertion hole 10a formed in the front surface plate 10 and the center of the back surface hole 11a formed in the back surface plate 11 are located on an extension line of the placing portion 31a of the holding base section 31. Therefore, the balloon catheter 50 having the shaft 51 placed on the placing portion 31a is inserted into the pleating section 2 through the center position of the insertion hole 10a.

In a state in which the support base 4 faces the front surface plate 20 of the folding section 3, the center of the insertion hole 20a formed in the front surface plate 20 and the center of the back surface hole 21a formed in the back surface plate 21 are located on an extension line of the placing portion 31a of the holding base section 31. For this reason, the balloon catheter 50 having the shaft 51 placed on the placing portion 31*a* is inserted into the folding section 3 through the center position of the insertion hole 20*a*.

Figure 3:
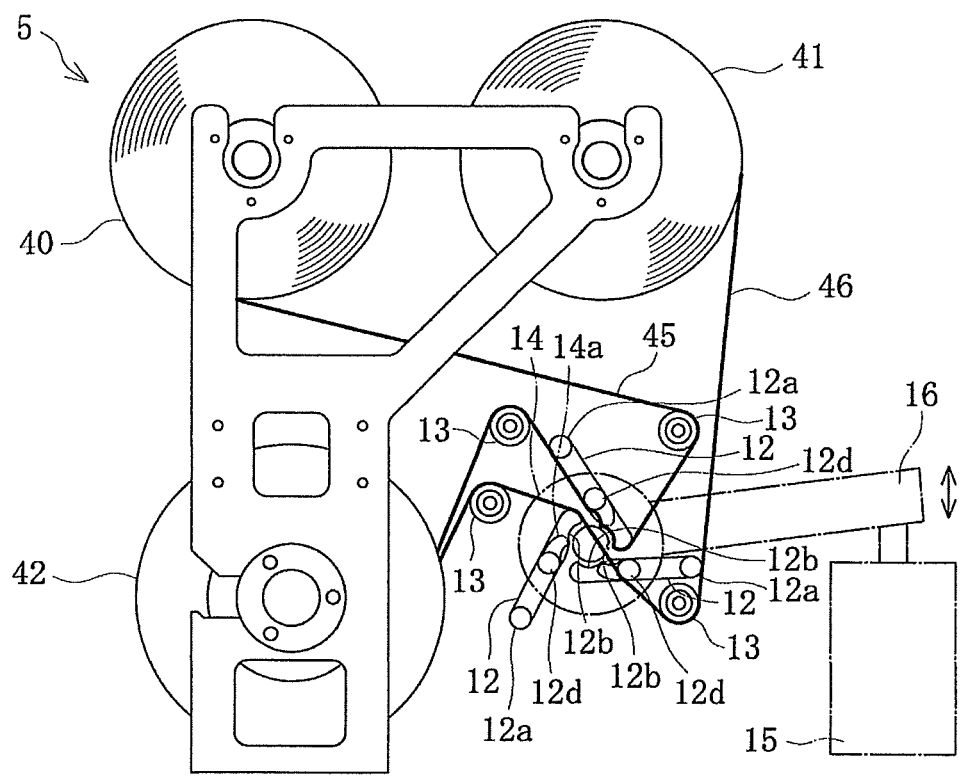
FIG. 3 is a front view depicting the layout of blades and a film supply section in a pleating section.

Now, the structure of the pleating section 2 will be described below. As depicted in FIG. 3, the pleating section 2 is provided therein with three blades 12. Each of the blades 12 is a plate-shaped member which is the same in sectional shape at each position along the axial direction of the balloon catheter 50 inserted. The blades 12 are disposed such that they are at an angle of 120° from one another, with the center position in regard of insertion of the balloon 52 as a reference. In other words, the blades 12 are disposed at regular and equal angular intervals along the circumferential direction. The blade 12 has a rotational center portion 12*a* near an outer circumferential end portion of the blade 12, and can be moved rotationally about the rotational center portion 12*a*. In addition, the blade 12 has a moving pin 12*d* extending in the axial direction, on the inner circumferential side of the rotational center portion 12*a*. The moving pin 12*d* is fitted in a fitting groove 14*a* formed in a rotary member 14 which is rotatable in the pleating section 2. The rotary member 14 is interlocked with a beam portion 16 extending substantially horizontally. The rotary member 14 is movable rotationally by receiving a rotating force from the beam portion 16 which is inclined by receiving a force from a drive source 15 such as a hydraulic cylinder or a motor. When the rotary member 14 is rotated, the moving pins 12*d* fitted in the fitting grooves 14*a* are moved in the circumferential direction, whereby each of the blades 12 is moved rotationally about the rotational center portion 12*a*. With the three blades 12 rotated, a space region in a central area surrounded by the blades 12 can be narrowed.

The blade 12 has a first shape forming portion 12*b* and a second shape forming portion 12*c* which are substantially arcuate in shape, at inner circumferential end portions on the side opposite to the rotational center portion 12*a*. Attendant on rotary movement of the blade 12, the first shape forming portion 12*b* makes contact with the surface of the balloon 52 inserted in the pleating section 2, whereby the balloon 52 can be formed with a pleat. Attendant on rotary movement of the blade 12, the second shape forming portion 12*c* makes contact with the pleat formed in the balloon 52, whereby the pleat can be curved in a predetermined direction. In addition, the pleating section 2 has a heater for heating the blades 12. The blades 12 may have a function of cooling.

The blades 12 are supplied with the first film 45 and the second film 46 which are formed of resin, from the film supplying section 5. For guiding each of the films, a plurality of rotary shaft portions 13 are provided in the pleating section 2. The first film 45 is supplied from a first film holding section 40 and through the rotary shaft portion 13 to be fed to a surface of the blade 12 disposed at an upper part. In addition, the first film 45 is fed through the blade 12 and the rotary shaft portion 13 to reach a film take-up section 42. The second film 46 is supplied from a second film holding section 41 and through the rotary shaft portion 13 to be fed to the two blades 12 disposed at lower parts. In addition, the second film 46 is fed through the rotary shaft portion 13 to reach the film take-up section 42. As a result of these, a center position of the pleating section 2 in which the balloon 52 is inserted is in the state of being surrounded by the first film 45 and the second film 46.

The first film 45 and the second film 46 have a protecting function for preventing direct contact of the balloon 52 with the surfaces of the blades 12 when the balloon 52 is inserted into the pleating section 2 and the blades 12 are moved rotationally to form the balloon 52 with pleats. After the pleats of the balloon 52 are formed, predetermined lengths of the first film 45 and the second film 46 are taken up by the film take-up section 42. In other words, the portions of the first film 45 and the second film 46 which portions have once made contact with the balloon 52 do not make contact with the balloon 52 again, and new portions of the films are supplied to the center position of the pleating section 2 every time the balloon (a new balloon) 52 is inserted.

Figure 5:
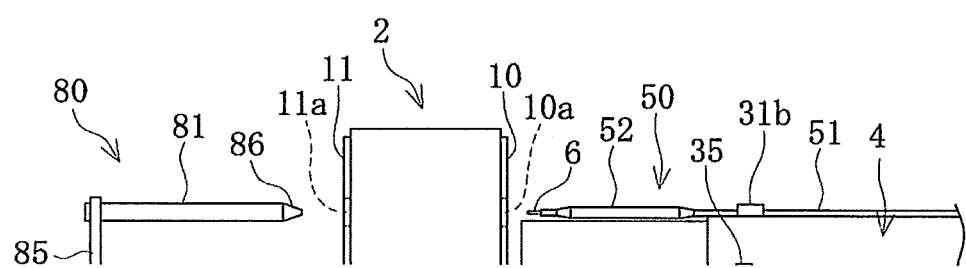
FIG. 5 is a side view depicting a support base and the pleating section.
Figure 6:
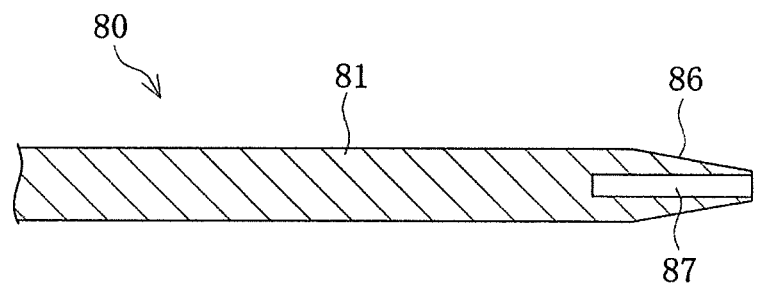
FIG. 6 is a cross-sectional view depicting a distal portion of an assisting shaft.

The structure of the first insertion assisting section 80 will now be described. As depicted in FIGS. 5 and 6, the pleating section 2 is provided with the first insertion assisting section 80 that assists insertion of the balloon catheter 50 into the insertion hole 10*a*. The first insertion assisting section 80 includes an elongated assisting shaft 81, an interlock portion 82 (see FIG. 13) interlocking the assisting shaft 81 with the support base 4, and support sections 83 (see FIG. 13) supporting the interlock portion 82 in a slidable manner. The interlock portion 82 includes an elongated interlock shaft 84, and a fixing section 85 that fixes the assisting shaft 81 and the interlock shaft 84 so that the interlock shaft 84 and the assisting shaft 81 move together. The interlock shaft 84 constitutes a part of the assisting shaft 81 that engages or interlocks with the interlock portion 33 and that is not inserted into or through the back surface hole 11*a*.

The assisting shaft 81 holds the core metal member 6 inserted in the balloon catheter 50, and restrains the balloon catheter 50 from bending. The assisting shaft 81 is also capable of holding (configured to hold) the shaft 51 of the balloon catheter 50. The assisting shaft 81 is circular in sectional shape of an outer peripheral surface, and can enter the back surface hole 11*a* of the pleating section 2 and project to the exterior through the insertion hole 10*a*. The assisting shaft 81 has, on the side facing the back surface plate 11, a decreasing diameter portion 86 decreasing in outside diameter toward the back surface plate 11 in a tapered manner. An end portion of the assisting shaft 81 on the side opposite to the decreasing diameter portion 86 is interlocked with the fixing section 85 extending in a direction orthogonal to the assisting shaft 81. The decreasing diameter portion 86 of the assisting shaft 81 is formed therein with a cavity portion 87 opening at a distal end surface of the decreasing diameter portion 86. An axis of the cavity portion 87 coincides with the axis of the assisting shaft 81. While the inside diameter of the cavity portion 87 is constant along the axis, but may not be constant; for example, the inside diameter may decrease toward the depth side. The core metal member 6 can be inserted into the cavity portion 87 through the opening. With the core metal member 6 inserted in the cavity portion 87, the core metal member 6 is supported by the assisting shaft 81. This makes it possible to insert a distal portion of the balloon catheter 50 between the first film 45 and the second film 46 which two films are located between the blades 12, while restraining bending of the balloon catheter 50 by the assisting shaft 81 and the core metal member 6.

An outside diameter of the assisting shaft 81 is greater than the outside diameter of the balloon 52 before wrapping of the held balloon catheter 50. This makes it possible to restrain the balloon 52 from making contact with the first film 45 and the second film 46, at the time of inserting the balloon 52 between the first film 45 and the second film 46. This makes is possible to restrain a drug on a surface of the balloon 52 from dropping off due to contact with the first film 45 or the second film 46.

The length of the assisting shaft 81 from the fixing section 85 to the distal end of the decreasing diameter portion 86 is preferably greater than the length in the extending direction of the blades 12 along the balloon catheter 50. This ensures that after the assisting shaft 81 passed through the blades 12 is caused to hold the core metal member 6, the assisting shaft 81 can be drawn out from between the blades 12 by retreating the assisting shaft 81. This permits the balloon 52 to be appropriately disposed between the plurality of blades 12. In addition, the length of the assisting shaft 81 from the fixing section 85 to the distal end of the decreasing diameter portion 86 is more preferably greater than the length from the insertion hole 10a to the back surface hole 11a. This permits the assisting shaft 81 to reach from the back surface hole 11a to the insertion hole 10a, and to be completely drawn out from the back surface hole 11a.

The interlock shaft 84 is parallel to the assisting shaft 81, and part of the interlock shaft 84 penetrates the pleating section 2. The interlock shaft 84 may not penetrate the pleating section 2. One end of the interlock shaft 84 is fixed to the assisting shaft 81 by the fixing section 85. The other end of the interlock shaft 84 can be interlocked with a holding base section 31 of the support base 4. The interlock shaft 84, by being interlocked with the holding base section 31, can be moved together with the holding base section 31. With the interlock shaft 84 moved together with the holding base section 31, the assisting shaft 81 also is moved together with the holding base section 31. Therefore, when the holding base section 31 holding the shaft 51 on the proximal side relative to the balloon 50 of the balloon catheter 50 is moved along the axial direction of the balloon catheter 50, the assisting shaft 81 supporting a distal portion of the balloon catheter 50 is thereby also moved together with the holding base section 31. For this reason, the balloon catheter 50 can be restrained from bending at the time of inserting the balloon catheter 50 into the pleating section 2.

The sectional shape of an outer peripheral surface of the interlock shaft 84 is not particularly limited, and is, for example, a rectangle. This ensures that the interlock shaft 84 is supported in a slidable but non-rotatable manner in relation to the support sections 83.

The support sections 83 are disposed on the base 1, and each have a support hole 83a penetrated by the interlock shaft 84. The support sections 83 support the interlock shaft 84 in a slidable manner. The number of the support sections 83 is not particularly limited.

The holding base section 31 is provided with a holding base side interlock portion 33 to which an end portion of the interlock shaft 84 can be interlocked. The holding base side interlock portion 33 has an accommodation hole 34 that accommodates a distal portion of the interlock shaft 84. In addition, the holding base side interlock portion 33 has a fixing screw 35 screwed into the inside of the accommodation hole 34 from a lateral side. With the fixing screw 35 screwed in in a state in which the interlock shaft 84 is accommodated in the accommodation hole 34, the interlock shaft 84 can be fixed to the holding base section 31. The method for interlocking the interlock shaft 84 and the holding base section 31 is not limited to the fixing screw 35. For example, the holding base side interlock portion may be a part against which the distal portion of the interlock shaft 84 only abuts. When the distal portion of the interlock shaft 84 abuts against the holding base side interlock portion, the interlock shaft 84 is moved by being pushed by the holding base side interlock portion when the holding base section 31 is moved toward the pleating section 2. In other words, even in a configuration in which the distal portion of the interlock shaft 84 only abuts against the holding base side interlock portion, the interlocked state at the time of movement can be maintained.

The structures of a distal portion of the shaft 51 and the balloon 52 will now be described. As depicted in FIG. 4, the shaft 51 includes a hollow outer tube 53, and a hollow inner tube 54. The inner tube 54 is accommodated in a hollow inside of the outer tube 53, and the shaft 51 is of a double-tube structure at the distal portion of the shaft 51. The hollow inside of the inner tube 54 forms a guide wire lumen 58 in and through which a guide wire may be inserted and passed. In addition, an inflation lumen 59 in which an inflation fluid for the balloon 52 flows is formed in the hollow inside of the outer tube 53 and on the outside of the inner tube 54. The inner tube 54 is open to the exterior at an opening portion 55.

The inner tube 54 protrudes to the distal side beyond a distal end of the outer tube 53. The balloon 52 has a proximal-side end portion fixed to a distal portion of the outer tube 53, and has a distal-side end portion fixed to a distal portion of the inner tube 54. As a result of this, the inside of the balloon 52 communicates with the inflation lumen 59. The balloon 52 can be inflated by injecting an inflation fluid into the balloon 52 through the inflation lumen 59. The inflation fluid may be either a gas or a liquid; for example, a gas such as helium gas, $CO_2$ gas and $O_2$ gas or a liquid such as a saline solution and a contrast medium can be used as the inflation fluid.

The outer tube 53 and the inner tube 54 are preferably formed from a material that has a certain degree of flexibility. Examples of such a material include polyolefins such as polyethylene, polypropylene, polybutene, ethylene-propylene copolymer, ethylene-vinyl acetate copolymer, ionomers, or mixtures of two or more of them, flexible polyvinyl chloride resin, polyamides, polyamide elastomers, polyesters, polyester elastomers, polyurethane, fluoro-resin such as polytetrafluoroethylene, silicone rubbers and latex rubbers.

As depicted in FIG. 4, the balloon catheter 50 to be inserted into the pleating section 2 has the shaft 51 placed on a placing portion 31a of the support base 4, and held and fixed by the holding portion 31b. In this instance, the shaft 51 is disposed in such a manner that the opening portion 55 is located on the proximal side relative to the holding portion 31b. While the distal side relative to the support base 4, of the shaft 51 including the balloon 52, is not supported from below, the core metal member 6 inserted in and passed through the guide wire lumen 58 is provided on the distal side relative to the opening portion 55. By virtue of the core metal member 6, the shaft 51 is restrained from bending due to its own weight.

The core metal member 6 is formed in a thin elongated wire-like shape or a hollow shape from a metallic material. As the metallic material for forming the core metal member 6, there is selected a material having such a degree of stiffness that a distal portion of the shaft 51 inclusive of the balloon 52 will not bend due to its own weight where the core metal member 6 is inserted in the balloon 52 and the shaft 51. The metallic material for forming the core metal member 6 is not specifically restricted, and examples thereof include stainless steel, Ni—Ti alloys, tungsten, and hard metals. In addition, the core metal member 6 may be formed by annealing any of these metallic materials, for realizing a shape memory property.

The core metal member 6 is formed in a substantially circular shape in section, and an outside diameter thereof is smaller than the inside diameter of the inner tube 54 by 0.01 to 0.1 mm. If the outside diameter of the core metal member 6 is smaller than the aforesaid appropriate value in relation to the inside diameter of the inner tube 54, the balloon 52 part cannot be held sufficiently by the core metal member 6 and bending of the balloon 52 would occur. As a result, the shaft 51 may be distorted when the balloon 52 is formed with pleats by the pleating section 2. In addition, if the outside shape of the core metal member 6 is greater than the aforesaid appropriate value in relation to the inside diameter of the inner tube 54, the core metal member 6 may interfere with the inner surface of the inner tube 54, possibly breaking the inner tube. With the outside diameter of the core metal member 6 set as above-mentioned, these problems can be prevented from occurring.

The core metal member 6 has such a length as to extend from the distal side relative to the distal end of the balloon 52 to the proximal side relative to the opening portion 55 of the shaft 51. Since the opening portion 55 is located on the proximal side relative to the holding portion 31b of the support base 4, the core metal member 6 also is held by the holding portion 31b at the position where the shaft 51 is held by the holding portion 31b. In other words, the core metal member 6 is held by the assisting shaft 81 on the distal side, and by the holding portion 31b of the support base 4 on the proximal side, whereby the shaft 51 can be more effectively restrained from bending due to its own weight.

In this way, by the core metal member 6, the shaft 51 is restrained from bending due to its own weight, with respect to the distal side relative to its portion supported by the support base 4. This permits the balloon 52 to be accurately positioned at, and inserted into, a center position of the pleating section 2. With the balloon 52 accurately positioned in relation to, and inserted into, the pleating section 2, the balloon 52 can be formed with the pleats accurately, and the pleats can be made uniform in the circumferential direction.

Figure 7:
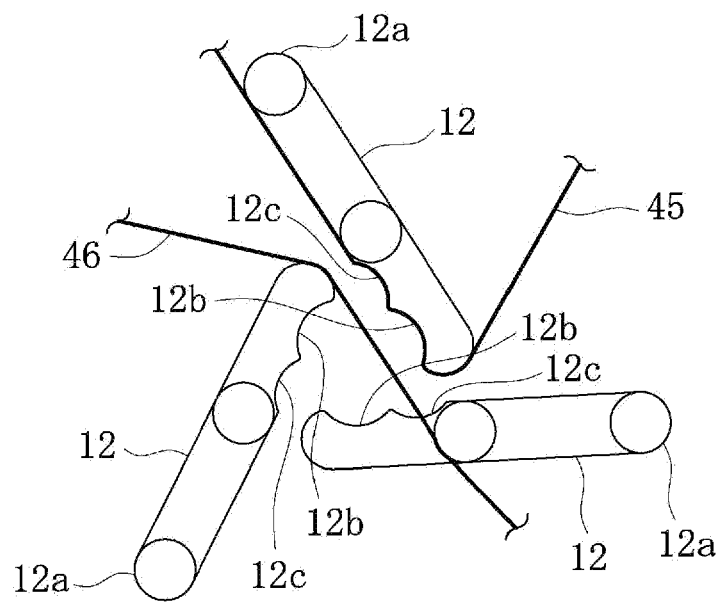
FIG. 7 is a front view of the blades in the pleating section.
Figure 10A:
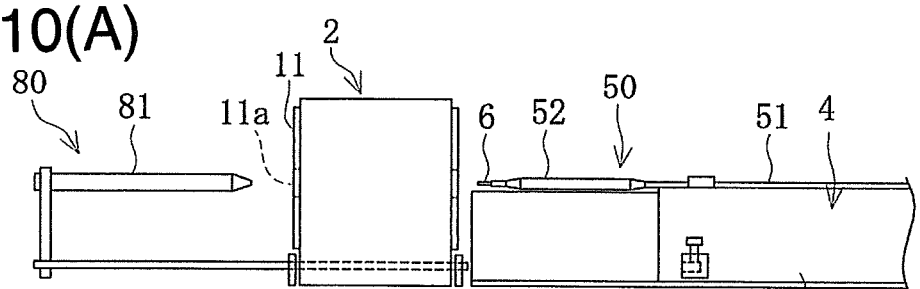

The pleating of the balloon 52 in the pleating section 2 will be described further. As depicted in FIG. 7, in a state before insertion of the balloon 52, first shape forming portions 12b and second shape forming portions 12c of the three blades 12 are in a mutually space-apart state. A central region between the blades 12 is surrounded by the first shape forming portions 12b which are substantially arcuate in shape. As depicted in FIG. 10(A), the assisting shaft 81 is not inserted in the back surface hole 11a of the back surface plate 11.

At the time of forming the balloon 52 with pleats, first, the shaft 51 of the balloon catheter 50 is mounted to the holding base section 31 of the support base 4. The inflation fluid is injected into the balloon 52 through a hub 56 and the inner tube 54, putting the balloon 52 into a somewhat inflated state.

Figure 8:
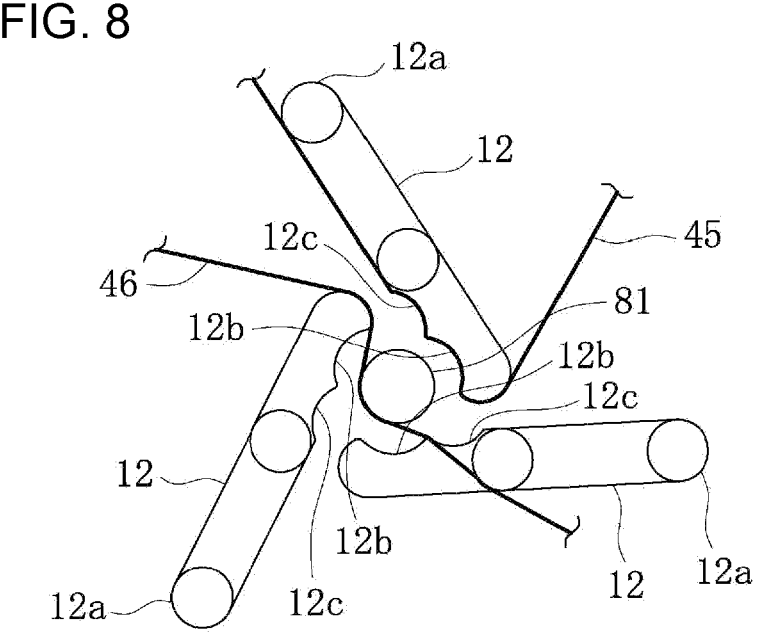
FIG. 8 is a front view of a state in which the assisting shaft is inserted in the pleating section.
Figure 10B:
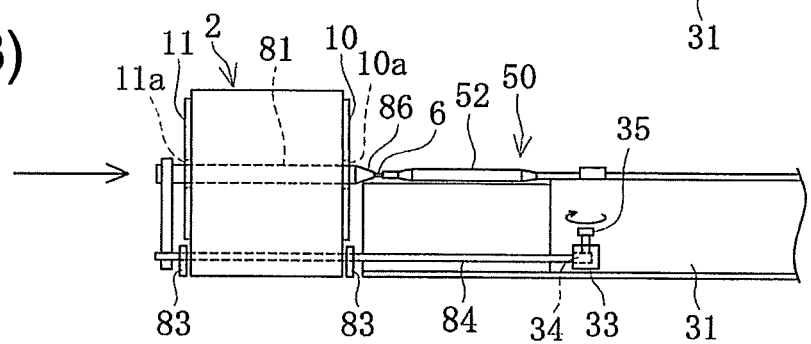

Next, as depicted in FIGS. 8 and 10(B), the assisting shaft 81 is inserted into the back surface hole 11a of the pleating section 2, and is protruded to the exterior through the insertion hole 10a. The interlock shaft 84 slides on the support sections 83, and its distal portion abuts against the holding base side interlock portion 33. In this instance, since the decreasing diameter portion 86 is formed at the distal portion of the assisting shaft 81, the decreasing diameter portion 86 can easily pass between the first film 45 and the second film 46. Therefore, the assisting shaft 81 can protrude to the exterior through the insertion hole 10a, without damaging the first film 45 or the second film 46. Next, the distal portion of the core metal member 6 protruding from the balloon catheter 50 is inserted into the cavity portion 87 of the assisting shaft 81. This puts the core metal member 6 into a state in which its distal portion is held by the assisting shaft 81. Subsequently, in a state in which the distal portion of the interlock shaft 84 is inserted or positioned in the accommodation hole 34 of the holding base side interlock portion 33, the fixing screw 35 is screwed in. By this, the interlock shaft 84 is interlocked with or fixed in position relative to the holding base section 31.

Figure 10C:
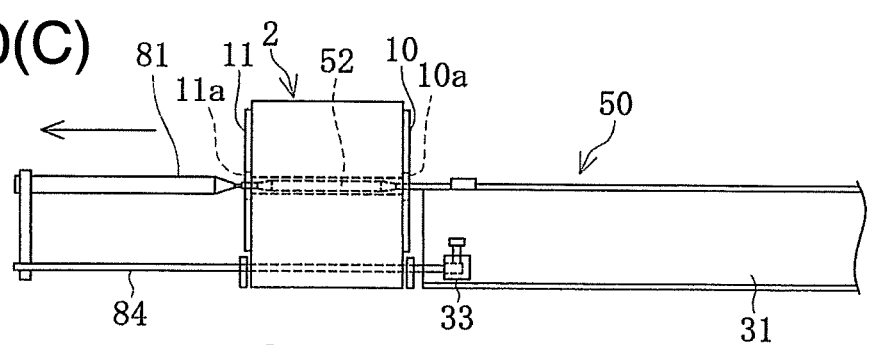

Next, as depicted in FIGS. 4 and 10(C), the holding base section 31 is moved toward the pleating section 2. In this instance, since the interlock shaft 84 is interlocked with the holding base section 31, the assisting shaft 81 also is moved together with the holding base section 31. For this reason, the balloon catheter 50 can be restrained from bending when the balloon catheter 50 is inserted into the pleating section 2. Therefore, the balloon 52 can be accurately positioned at a center position of the pleating section 2. Accordingly, the pleats of the balloon 52 can be formed uniformly in the circumferential direction. In addition, since the outside diameter of the assisting shaft 81 is greater than the outside diameter of the balloon 52, the balloon 52 can be restrained from making contact with the first film 45 or the second film 46. As a result of this, the drug can be restrained from dropping off the balloon 52. When the assisting shaft 81 reaches the exterior of the pleating section 2 by passing through the back surface hole 11a, the balloon 52 is located in the central region between the blades 12. Subsequently, the heated blades 12 of the pleating section 2 are rotated, whereby the balloon 52 is formed with the pleats.

Figure 9:
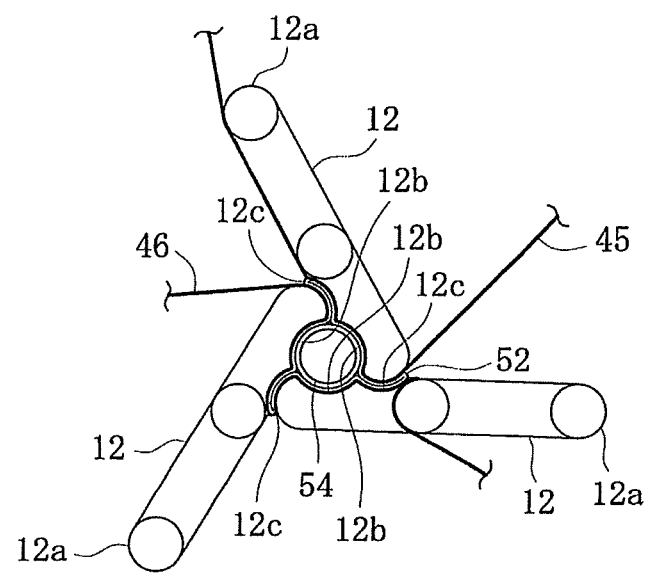
FIG. 9 is a front view of the blades in a state in which the blades are rotated from the state of FIG. 7 to form the balloon with pleats.

When the blades 12 are rotated, the first shape forming portions 12b of the blades 12 come closer to one another, and the central region between the blades 12 is narrowed, as depicted in FIG. 9. Attendant on this, the balloon 52 inserted in the central region between the blades 12 is pressed against the inner tube 54 by the first shape forming portions 12b. A portion of the balloon 52 not pressed by the first shape forming portion 12b is pushed out into a gap between a distal portion of one blade 12 and the second shape forming portion 12c of the blade 12 adjacent to the one blade 12, whereby a pleat curved to one side is formed. Since the balloon 52 is heated by the blades 12, the pleats thus formed can be maintained in their shape. In this way, the balloon 52 is formed with three pleats in the circumferential direction. In the case where a surface of the balloon 52 is provided thereon with a coating which is low in resistance to heat, the blades 12 may not be heated, or may be cooled.

In this instance, surfaces of the blades 12 which surfaces make contact with the balloon 52 are covered with the first film 45 and the second film 46, so that the balloon 52 does not make direct contact with the surfaces of the blades 12. After the balloon 52 is formed with the pleats, the blades 12 are moved rotationally in the manner of being returned to their original positions. In the process of pleating, a step of excessively inflating the balloon 52 and then deflating the balloon 52 a little or a step of inflating the balloon 52 while avoiding excessive inflation and then deflating the balloon 52 a little may be provided.

Figure 10D:
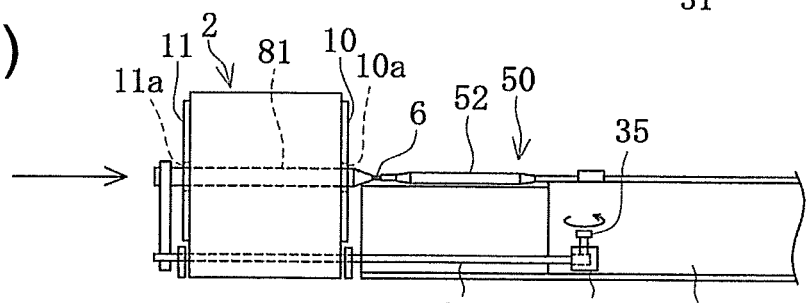

Next, as depicted in FIG. 10(D), the holding base section 31 is moved, and the balloon 52 is drawn out of the pleating section 2. In this instance, since the interlock shaft 84 is interlocked with the holding base section 31, the assisting shaft 81 also is moved together with the holding base section 31. Therefore, bending of the balloon catheter 50 can be restrained by the assisting shaft 81 and the core metal member 6. Consequently, the balloon 52 can be restrained from making contact with the insertion hole 10a or the like in the pleating section 2, and the drug can be restrained from dropping off.

Figure 10E:
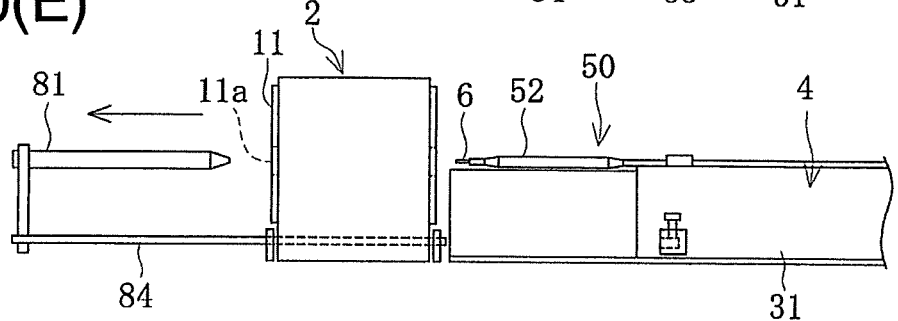

Thereafter, the fixing screw 35 at the holding base side interlock portion 33 is loosened, to release the interlock between the holding base section 31 and the interlock shaft 84. Subsequently, as depicted in FIG. 10(E), the assisting shaft 81 is moved, to be drawn out from the back surface hole 11a of the pleating section 2. In this instance, the core metal member 6 is drawn out of the cavity portion 87 of the assisting shaft 81. By this, the support base 4 can be moved on the base 1, and the holding base section 31 is oriented toward the folding section 3. The interlock between the holding base section 31 and the interlock shaft 84 may be released before drawing the balloon 52 out of the pleating section 2. In this case, the balloon catheter 50 is drawn out of the pleating section 2, while being restrained by the core metal member 6 from bending.

Figure 11:
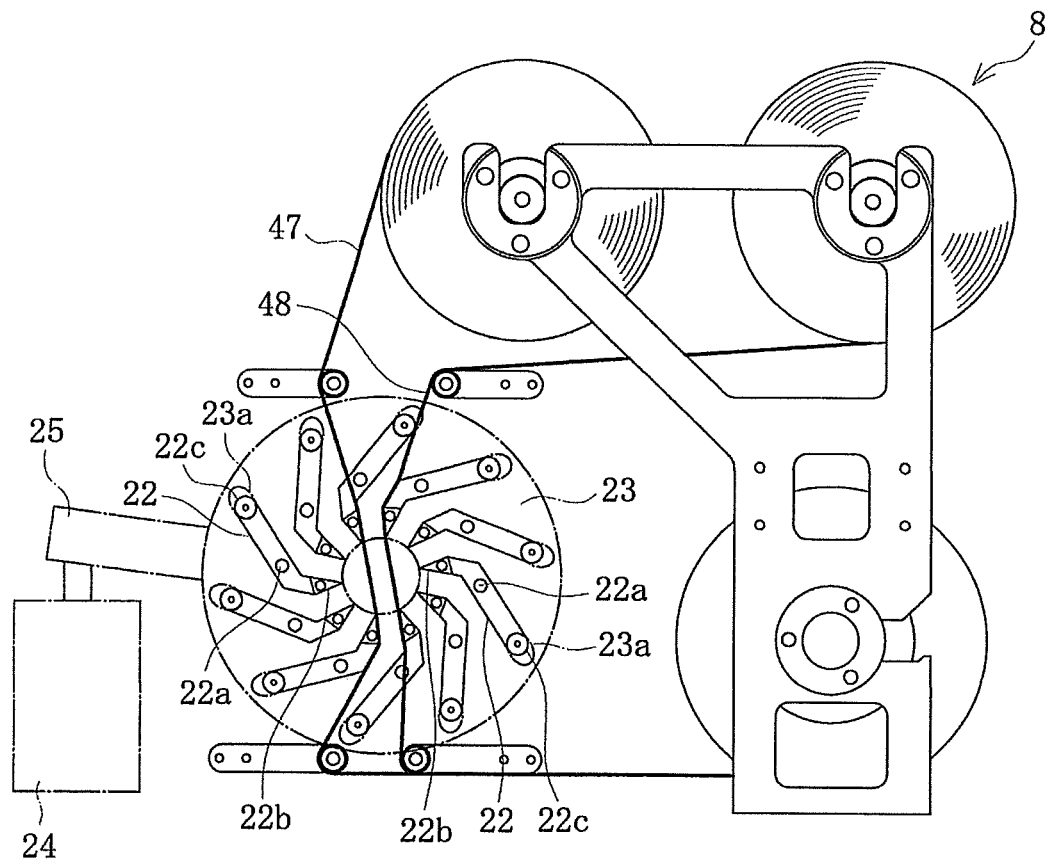
FIG. 11 is a front view depicting the layout of the blades and a film supply section in a folding section.

Now, the structure of the folding section 3 will be described below. As depicted in FIG. 11, the folding section 3 is provided therein with ten blades 22. Each of the blades 22 is a plate-shaped member formed to be the same in sectional shape at each position along the axial direction of the balloon catheter 50 to be inserted. The blades 22 are disposed such that they are at an angle of 36° from one another, with the center position in regard of insertion of the balloon as a reference. In other words, the blades 22 are disposed at regular (equal) angular intervals along the circumferential direction. The blade 22 has a rotational center portion 22a near an outer circumferential end portion of the blade 22, and can be moved rotationally about the rotational center portion 22a. In addition, the blade 22 has a moving pin 22c extending in the axial direction, near a substantially outer circumferential end portion of the blade 22. The moving pin 22c is fitted in a fitting groove 23a formed in a rotary member 23 which is rotatable in the folding section 3. The rotary member 23 is interlocked with a beam portion 25 extending substantially horizontally. The rotary member 23 is movable rotationally by receiving a rotating force from the beam portion 25 which is inclined by receiving a force from a drive source 24 such as a hydraulic cylinder or a motor. When the rotary member 23 is rotated, the moving pins 22c fitted in the fitting grooves 23a are moved in the circumferential direction, whereby each of the blades 22 is moved rotationally about the rotational center portion 22a. With the ten blades 22 moved rotationally, a space region in a central area surrounded by the blades 22 can be narrowed.

The blade 22 is bent on the distal side, and has a distal portion 22b in a pointing shape. Attendant on rotary movement of the blade 22, the distal portion 22b makes contact with a surface of the balloon 52 inserted in the folding section 3, whereby the pleat formed in the balloon 52 can be folded in the manner of winding the pleats around the inner tube 54. In addition, the folding section 3 has a heater for heating the blades 22. The blades 22 may have a function of cooling.

The blades 22 are supplied with a first film 47 and a second film 48 from a film supplying section 8. The film supplying structure is the same as in the case of the pleating section 2. The first film 47 and the second film 48 are disposed opposite to each other in such a manner as to sandwich a central space region surrounded by the blades 22. By the first film 47 and the second film 48, the balloon 52 inserted in the folding section 3 can be prevented from making direct contact with the surfaces of the blades 22.

Figure 13:
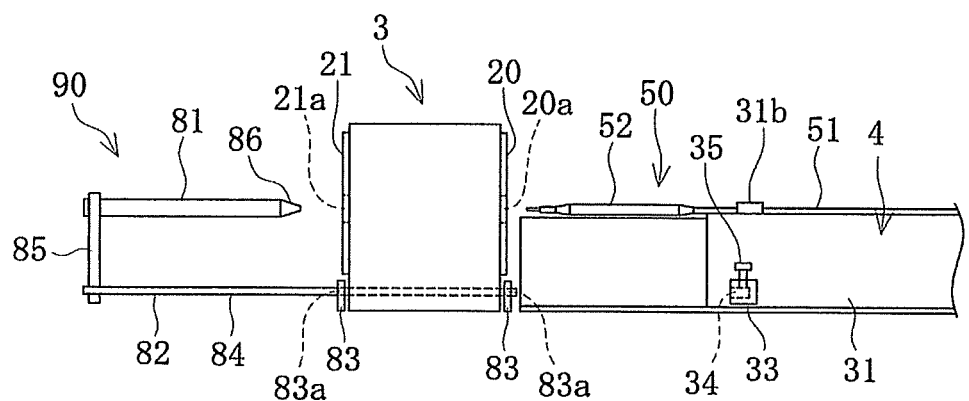
FIG. 13 is a side view depicting the support base and the folding section.

The second insertion assisting section 90 will now be described. As depicted in FIG. 13, the folding section 3 is provided with the second insertion assisting section 90 that assists insertion of the balloon catheter 50 into the insertion hole 20a. The second insertion assisting section 90 is similar in structure to the first insertion assisting section 80. Therefore, component members of the second insertion assisting section 90 are denoted by similar reference symbols to those for the first insertion assisting section 80, and descriptions of them will be omitted. The assisting shaft 81 of the second insertion assisting section 90 can enter the folding section 3 via the back surface hole 21a and can protrude to the exterior through the insertion hole 20a.

The outside diameter of the assisting shaft 81 is greater than the outside diameter after pleating of the balloon 52 of the held balloon catheter 50. This ensures that the balloon 52 is restrained from making contact with the first film 47 or the second film 48 when the balloon 52 is inserted between the first film 47 and the second film 48. As a result, the drug on the surface of the balloon 52 can be restrained from dropping off due to contact with the first film 47 or the second film 48.

The length from the assisting shaft 81 from the fixing section 85 to the distal portion is preferably greater than the extending length of the blades 22 along the balloon catheter 50. This ensures that after the core metal member 6 is held by the assisting shaft 81 passed through the blades 22, the assisting shaft 81 can be retreated and thereby drawn out from between the blades 22. As a result, the balloon 52 can be suitably disposed between the plurality of blades 22. In addition, the length of the assisting shaft 81 from the fixing section 85 to the distal end of the decreasing diameter portion 86 is more preferably greater than the length from the insertion hole 20a to the back surface hole 21a. This permits the assisting shaft 81 to reach from the back surface hole 21a to the insertion hole 20a, and to be completely drawn out from the back surface hole 21a.

Figure 14:
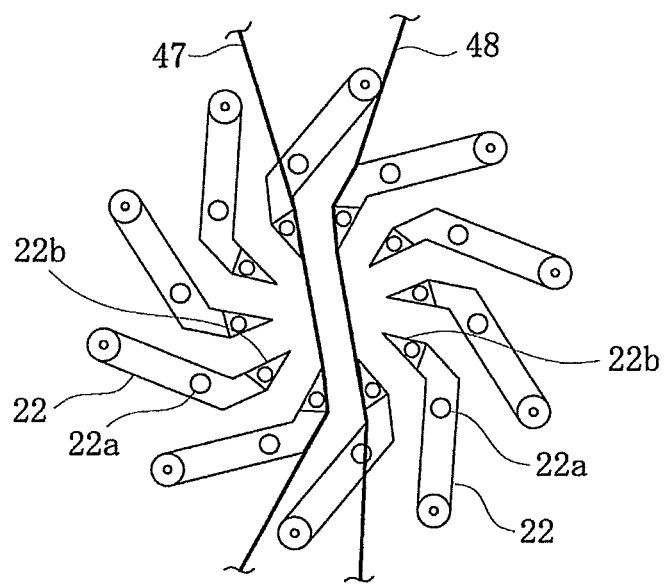
FIG. 14 is a front view of the blades in the folding section.
Figure 17A:
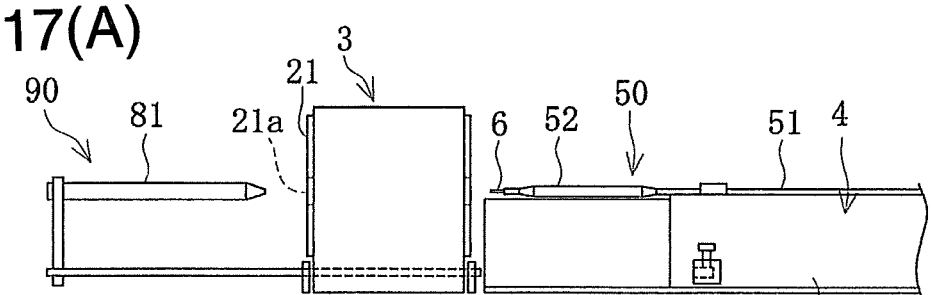
FIGS. 17(A)-17(E) depict side views for explaining a pleat wrapping operation and an operation of the assisting shaft provided in the folding section, wherein FIG. 17(A) (A) depicts a state before the balloon catheter is supported by the assisting shaft.

The folding of the balloon 52 in the folding section 3 will be described. After the balloon 52 is formed with the pleats in the pleating section 2 as aforementioned, the balloon catheter 50 is directed toward the folding section 3 together with the holding base section 31 by a movement of the support base 4. The shaft 51 of the balloon catheter 50 is in a state of being held by the holding portion 31b of the support base 4. The core metal member 6 is inserted in and passed through the balloon 52. As depicted in FIG. 14, in a state before insertion of the balloon 52, the distal portions 22b of the blades 22 are mutually spaced apart in the circumferential direction. The balloon 52 formed with the pleats can be inserted into a central region surrounded by the blades 22 and between the first film 47 and the second film 48. As depicted in FIG. 17(A), the assisting shaft 81 is not inserted in the back surface hole 21a of the back surface plate 21.

Figure 15:
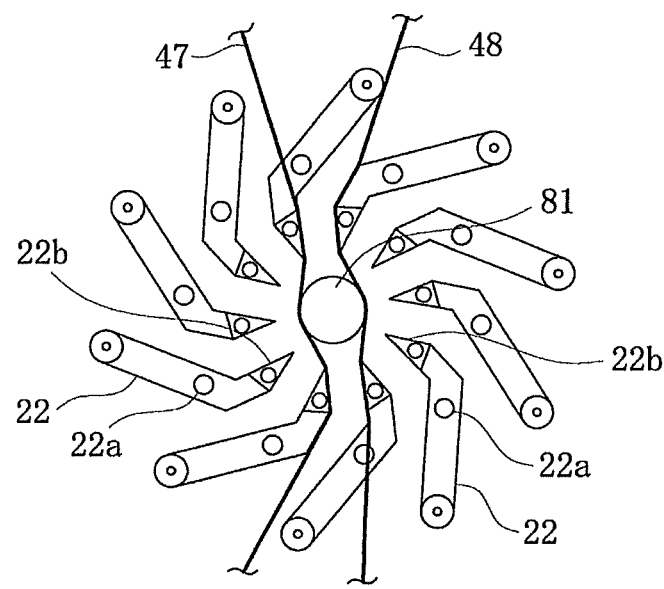
FIG. 15 is a front view of a state in which the assisting shaft is inserted in the folding section.
Figure 17B:
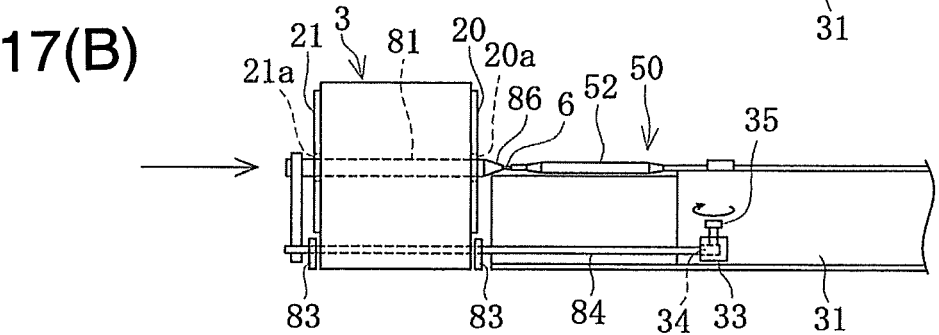

Next, as depicted in FIGS. 15 and 17(B), the assisting shaft 81 is inserted into the back surface hole 21a of the folding section 3, and is protruded to the exterior through the insertion hole 20a. The interlock shaft 84 slides on the support section 83, and its distal portion abuts against the holding base side interlock portion 33. In this instance, since the decreasing diameter portion 86 is formed at the distal portion of the assisting shaft 81, the decreasing diameter portion 86 can easily pass between the first film 47 and the second film 48. Therefore, the assisting shaft 81 can protrude to the exterior through the insertion hole 20a, without damaging the first film 47 or the second film 48. Subsequently, a distal portion of the core metal member 6 protruding from the balloon catheter 50 is inserted into the cavity portion 87 of the assisting shaft 81. This puts the core metal member 6 into a state in which its distal portion is held by the assisting shaft 81. Next, in a state in which the distal portion of the interlock shaft 84 is inserted in the accommodation hole 34 of the holding base side interlock portion 33, the fixing screw 35 is screwed in. As a result of this, the interlock shaft 84 is interlocked with the holding base section 31.

Figure 17C:
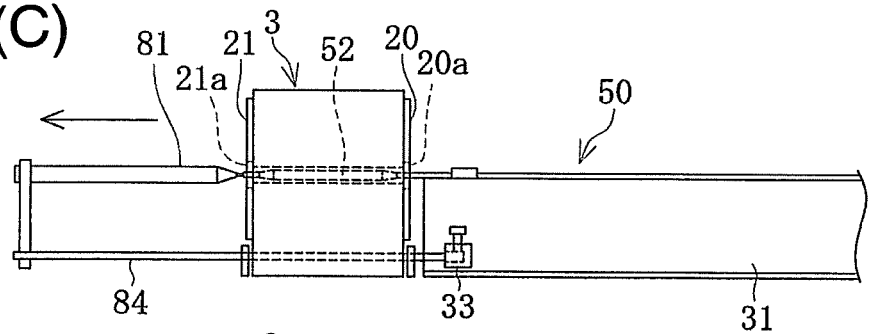

Subsequently, as depicted in FIGS. 12 and 17(C), the holding base section 31 is moved toward the folding section 3. In this instance, since the interlock shaft 84 is interlocked with the holding base section 31, the assisting shaft 81 also is moved together with the holding base section 31. For this reason, the balloon catheter 50 can be restrained from being bent when the balloon catheter 50 is inserted into the folding section 3. Therefore, the balloon 52 can be accurately positioned at the center position of the folding section 3. In addition, since the outside diameter of the assisting shaft 81 is greater than the outside diameter of the balloon 52, the balloon 52 can be restrained from making contact with the first film 47 or the second film 48. Consequently, the drug can be restrained from dropping off the balloon 52. When the assisting shaft 81 reaches the exterior of the folding section 3 by passing through the back surface hole 21a, the balloon 52 is located in the central region between the blades 22.

Figure 16:
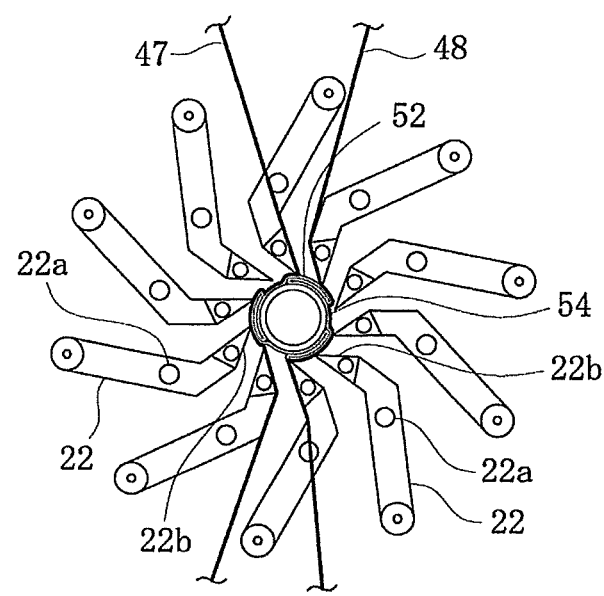
FIG. 16 is a front view of the blades in a state in which the blades are rotated from the state of FIG. 14 to fold the pleats of the balloon.

Next, as depicted in FIG. 16, the folding section 3 is moved rotationally. When the blades 22 are moved rotationally, the distal portions 22b of the blades 22 come closer to one another, and the central region between the blades 22 is narrowed. Attendant on this, the balloon 52 inserted in the central region between the blades 22 is put into a state in which the pleats are laid flat in the circumferential direction by the distal portions 22b of the blades 22. Since the blades 22 are preliminarily heated before insertion of the balloon 52 and the balloon 52 is heated by the blades 22, the pleats laid flat in the circumferential direction by the blades 22 can be maintained in their shape. The blades 22 may be preliminarily cooled.

In this instance, the surfaces of the blades 22 which surfaces make contact with the balloon 52 are covered with the first film 47 and the second film 48, so that the balloon 52 does not make direct contact with the surfaces of the blades 22. Since the balloon catheter 50 is restrained by the core metal member 6 and the assisting shaft 81 from bending, the balloon 52 is accurately positioned at the center position of the folding section 3. Therefore, generation of back folding at the time of folding the balloon 52 can be restrained. After the pleats of the balloon 52 are folded, the blades 22 are moved rotationally in the manner of being returned to their original positions.

Figure 17D:
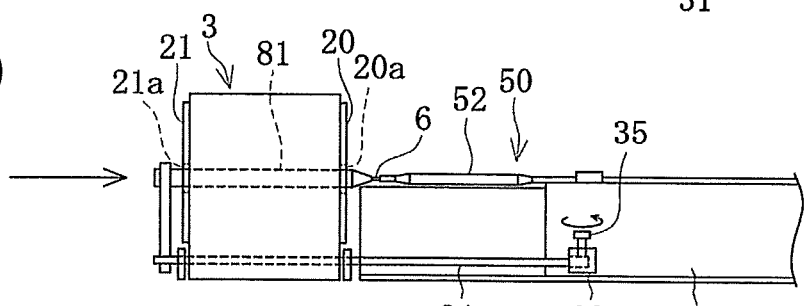

Next, as depicted in FIG. 17(D), the holding base section 31 is moved, whereby the balloon 52 is withdrawn from the folding section 3. In this instance, since the interlock shaft 84 is interlocked with the holding base section 31, the assisting shaft 81 is also moved together with the holding base section 31. Therefore, the balloon catheter 50 can be restrained by the assisting shaft 81 and the core metal member 6 from bending. Accordingly, the balloon 52 can be restrained from making contact with the insertion hole 20a or the like in the folding section 3, and the drug can be prevented from dropping off.

Figure 17E:
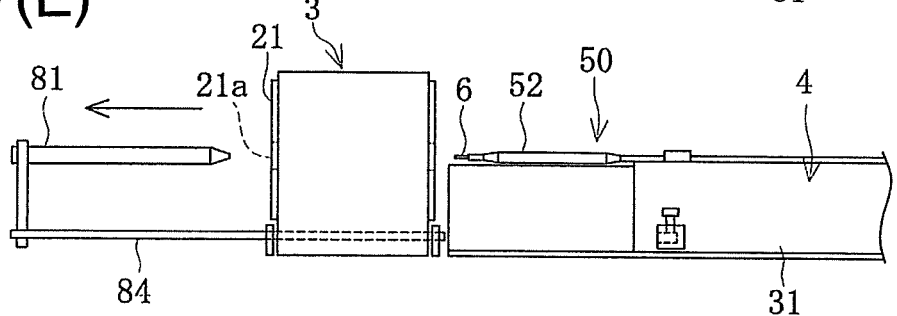

Thereafter, the fixing screw 35 of the holding base side interlock portion 33 is untightened, to release the interlock between the holding base section 31 and the interlock shaft 84. Subsequently, as depicted in FIG. 17(E), the assisting shaft 81 is moved, to be withdrawn from the back surface hole 21a of the folding section 3. By this, the wrapping of the balloon 52 by the balloon wrapping apparatus is completed. The interlock between the holding base section 31 and the interlock shaft 84 may be released before withdrawing the balloon 52 from the folding section 3. In this case, the balloon catheter 50 is withdrawn from the folding section 3 while being restrained by the core metal member 6 from bending.

While a case in which the balloon 52 of a rapid exchange type catheter is wrapped by the balloon wrapping apparatus has been described above, a balloon 62 of an over-the-wire type catheter can also be wrapped by the same balloon wrapping apparatus.

Figure 18:
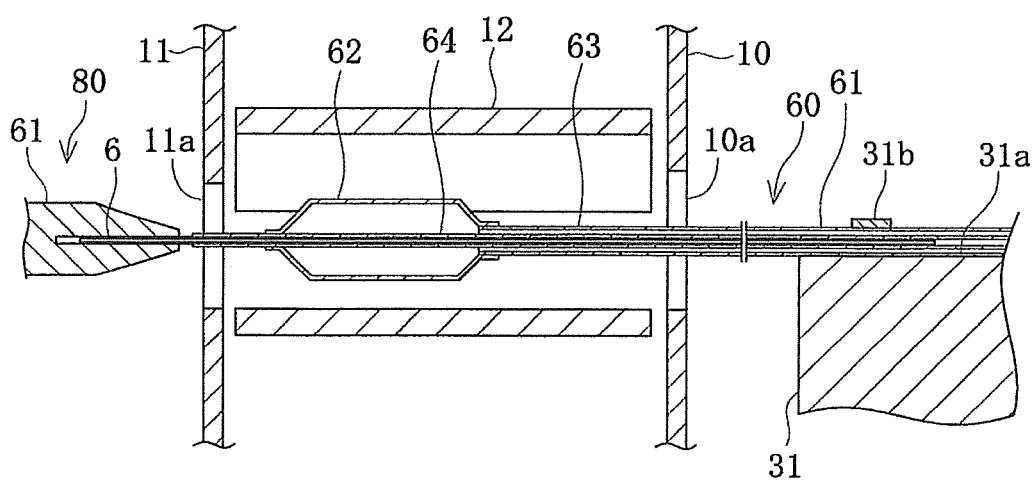
FIG. 18 is a cross-sectional view of a balloon catheter and a pleating section in a state in which a balloon is inserted in the pleating section, for an over-the-wire type balloon catheter.

As depicted in FIG. 18, this over-the-wire type balloon catheter 60 has a balloon 62 at a distal-side end portion of a shaft 61. The shaft 61 has a configuration in which, for the whole length on the proximal side relative to the balloon 62, an inner tube 64 is disposed in a hollow inside of an outer tube 63, and the outer tube 63 and the inner tube 64 extend to a hub provided at a proximal-side end portion of the shaft 61. The structure of the balloon 62 part is similar to that in the case of the rapid exchange type.

Figure 19:
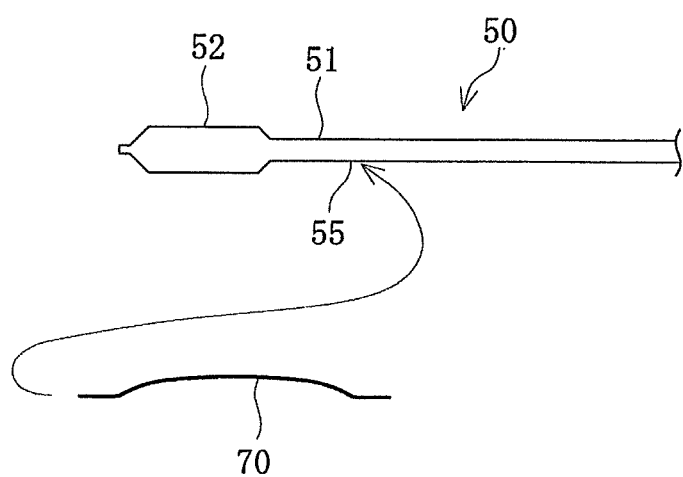
FIG. 19 is a front view of a core metal member and a balloon catheter in a second mode.

An assisting shaft 100 and a core metal member 70 in a second mode will now be described. As depicted in FIG. 19, the core metal member 70 is formed such that an intermediate portion is curved. In FIG. 19, the core metal member 70 is inserted into the rapid exchange type balloon catheter 50 drawn on the upper side. The core metal member 70 is curved in such a manner that when the core metal member 70 is inserted in the balloon catheter 50, a part located in the shaft 51 is projected to the upper side.

Figure 20:
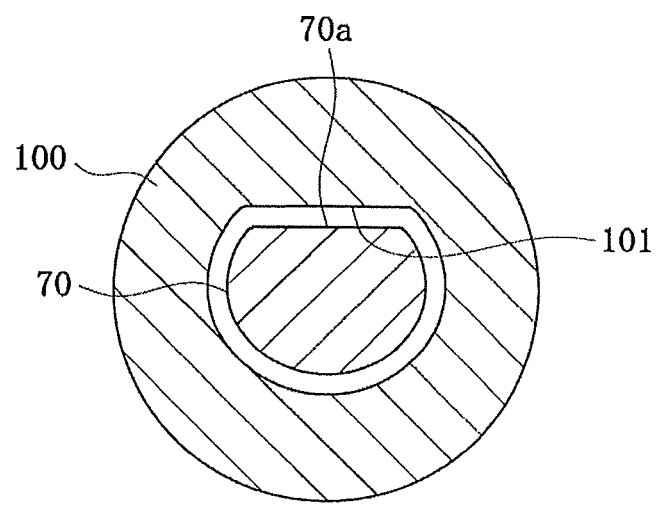
FIG. 20 is a cross-sectional view depicting an assisting shaft and a distal portion of the core metal member in the second mode.

As depicted in FIG. 20, at least a distal portion of the core metal member 70 has a flat surface portion 70a at part of a circumferential surface. The core metal member 70 in the present mode has its distal portion fixed to the assisting shaft 100, like in the aforementioned embodiment. That part of the assisting shaft 100 which fixes the core metal member 70 has a flat surface portion 101 corresponding to the flat surface portion 70a, and the core metal member 70 can be fixed in only a predetermined orientation in relation to the assisting shaft 100. This permits the core metal member 70 inserted in the shaft 51 to be in a predetermined orientation, specifically, an orientation in which the curved portion is projected to the upper side.

The core metal member 70 has a curvature corresponding to an amount of bending at a distal portion of the shaft 51 due to its own weight. Therefore, in a state in which the core metal member 70 is inserted in the shaft 51, the downward bending of the shaft 51 due to its own weight and the upward curvature of the core metal member 70 cancel each other, whereby the shaft 51 is put in a more horizontal state.

In this way, where the part of the core metal member 70 which part is inserted in the shaft 51 is provided with curvature, bending of the shaft 51 due to its own weight can be restrained more securely, and an effect of forming the pleats uniform in the circumferential direction in the pleating section 2 and an effect of restraining back folding in the folding section 3 can be further enhanced. The core metal member in a curved shape is not limited to the case of the rapid exchange type balloon catheter 50, but may be applied also to the over-the-wire type balloon catheter 60.

Figure 21:
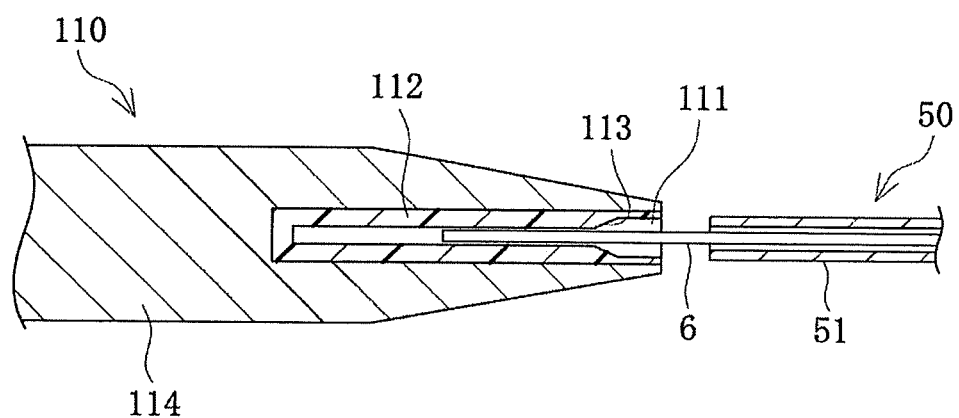
FIG. 21 is a cross-sectional view depicting an assisting shaft and a distal portion of a core metal member in a third mode.

An assisting shaft 110 in a third mode will now be described. As depicted in FIG. 21, a cavity portion 111 of the assisting shaft 110 in the present mode is formed in a hollow inner surface member 112 formed from a material having a high frictional coefficient. This makes it possible to restrain slippage of the core metal member 6 or the shaft 51 of the balloon catheter 50 inserted into the cavity portion 111, and favorably hold them on an assisting shaft 81. The material having a high frictional coefficient is higher in static frictional coefficient and dynamic frictional coefficient than a shaft main body 114 of the assisting shaft 110 into which the inner surface member 112 is fitted. Examples of the material having a high frictional coefficient include silicone rubbers, latex rubbers and natural rubber.

In addition, the inner surface member 112 may be an elastic material capable of elastic deformation. This ensures that the core metal member 6 or the shaft 51 of the balloon catheter 50 inserted into the cavity portion 111 can be held in the manner of being sandwiched by the inner surface member 112 which is elastically deformed. Examples of the elastic material include silicone rubbers, latex rubbers and natural rubber.

In addition, the cavity portion 111 of the assisting shaft 110 may decrease in inside diameter toward the depth side. This ensures that by pushing the core metal member 6 or the shaft 51 of the balloon catheter 50 into the cavity portion 111, the shaft 51 can be highly accurately positioned at the center of the assisting shaft 110, and can be favorably held by being sandwiched by the cavity portion 111. Therefore, the pleats of the balloon 52 can be formed uniformly in the circumferential direction in the pleating section 2, and generation of back folding can be restrained at the time of folding the pleats in the folding section 3.

The assisting shaft may have a mechanism for clamping and fixing the core metal member 6. Examples of the mechanism for clamping and fixing the core metal member 6 include a collet chuck, a scroll chuck, a drill chuck, and an independent chuck. In addition, the support base that supports the balloon catheter 50 may have a structure capable of rotation around an axis of the balloon catheter 50 in a state of holding the balloon catheter 50. In this case, by rotating the balloon catheter 50 in a direction reverse to a folding direction at the time of folding the pleats of the balloon 52 in the folding section 3, an effect of restraining back folding can be further enhanced.

As described above, the balloon wrapping apparatus according to the present embodiment is a balloon wrapping apparatus for wrapping the balloon 52 provided at a distal portion of the elongated shaft 51, and includes: the pleating section 2 for forming the balloon 52 with the pleats; the folding section 3 for folding the pleats formed in the balloon 52, along the circumferential direction; and the support base 4 that supports the shaft 51, can be moved closer to and away from at least one of the pleating section 2 and the folding section 3 (i.e., can be moved toward and away from: i) the pleating section 2; ii) the folding section 3; or iii) both the pleating section 2 and the folding section 3), and causes the balloon 52 to be insertable into the pleating section 2 and the folding section 3. The pleating section 2 and the folding section 3 include the insertion holes 10a and 20a into which the balloon 52 can be inserted, and the back surface holes 11a and 21a that are provided in the back surfaces on the sides opposite to the sides where the insertion holes 10a and 20a are provided and that communicate and are aligned with the insertion holes 10a and 20a. The pleating section 2 and the folding section 3 include: the assisting shaft 81 that can be inserted into the back surface holes 11a and 21a from the back surface side; and the interlock portion 82 interlocking a part of the assisting shaft 81 which part is not inserted in the back surface hole 11a or 21a with the support base 4 in such a manner that the assisting shaft 81 can be moved together with the support base 4. The assisting shaft 81 is formed with the cavity portion 87 from the side of facing the back surface hole 11a or 21a. The balloon wrapping apparatus configured as above-mentioned has a configuration in which by inserting the assisting shaft 81 into the back surface hole 11a or 21a and causing the assisting shaft 81 to reach the insertion hole 10a or 20a, the core metal member 6 inserted in the shaft 51 can be inserted in and held by the cavity portion 87 of the assisting shaft 81. Further, where the assisting shaft 81 is interlocked with the support base 4 by the interlock portion 82, the assisting shaft 81 is moved together with the support base 4, and, therefore, the balloon 52 can be inserted into the insertion hole 10a or 20a while maintaining the state in which the balloon 52 is held by the assisting shaft 81. This ensures that the distal portion of the shaft 51 of the balloon catheter 50 is supported by the assisting shaft 81 in such a manner as not to bend, and, therefore, the balloon 52 can be accurately positioned in relation to and inserted into the pleating section 2 and the folding section 3. Accordingly, the pleats of the balloon 52 can be formed uniformly in the circumferential direction in the pleating section 2, and generation of back folding can be restrained at the time of folding the pleats in the folding section 3.

In addition, the balloon wrapping apparatus further includes the core metal member 6 to be inserted in the shaft 51, and the core metal member 6 can be inserted into the cavity portion 87 of the assisting shaft 81. This ensures that by the combination of the assisting shaft 81 and the core metal member 6, the distal portion of the shaft 51 can be supported more securely in such a manner as not to bend. Therefore, the balloon 52 can be accurately positioned in relation to and inserted into the pleating section 2 and the folding section 3.

At least one of the pleating section 2 and the folding section 3 (i.e., the pleating section 2, the folding section 3, or both the pleating section 2 and the folding section 3) includes the plurality of blades 12, 22 aligned in the circumferential direction for giving a shape to the balloon 52, and the two films passing through a central portion surrounded by the plurality of blades 12, 22. The assisting shaft 81 has the decreasing diameter portion 86 decreasing in outside diameter toward the back surface hole 11a, 21a. This permits the decreasing diameter portion 86 of the assisting shaft 81 to smoothly pass between the two films.

In addition, the blades 12, 22 extend in a direction from the insertion hole 10a, 20a toward the back surface hole 11a, 21a, and the direction in which the assisting shaft 81 can be moved together with the support base 4 is parallel to the extending direction of the blades 12, 22. This permits the balloon 52 supported by the assisting shaft 81 to be accurately positioned at a central portion of the blades 12, 22. With the balloon 52 accurately positioned at the central portion of the blades 12, 22, the pleats of the balloon 52 can be formed uniformly in the circumferential direction in the pleating section 2, and generation of back folding can be restrained at the time of folding the pleats in the folding section 3.

The maximum outer diameter of the assisting shaft 81 is greater than the outer diameter of the balloon 52 when the balloon is being axially moved. This ensures that when the balloon 52 held by the assisting shaft 81 is moved in the axial direction together with the assisting shaft 81, the balloon 52 can be restrained from making contact with other members or parts. Therefore, the drug on the surface of the balloon 52 can be restrained from dropping off.

In addition, the core metal member 6 is longer than the length in the extending direction of the blades by not less than 10 mm. This permits the core metal member 6 to be placed on both the assisting shaft 81 and the support base 4, and the shaft 51 of the balloon catheter 50 can be securely supported and restrained from bending.

Note that the present invention is not limited only to the aforementioned embodiments, and various modifications can be made within the technical thought of the present invention by a person skilled in the art.

EXAMPLES

Examples according to the disclosure here and Comparative Examples will be described below. Drug-coated balloons of Examples 1 to 17 and Comparative Example 1 were produced under the conditions set forth in Tables 1 to 4 below.

TABLE 1

| Conditions | Example 1 | Example 2 | Example 3 | Example 4 | Example 5 |
|---|---|---|---|---|---|
| Diameter/length of balloon | 2.0 mm/40 mm | 4.0 mm/200 mm | 3.0 mm/200 mm | 2.0 mm/200 mm | 6.0 mm/200 mm |
| Material of balloon | Nylon | Nylon | Nylon | Nylon | Nylon |
| Surface condition of balloon catheter | Smooth, non-porous | Smooth, non-porous | Smooth, non-porous | Smooth, non-porous | Smooth, non-porous |
| Specification of guide wire lumen | 0.014 inch | 0.014 inch | 0.014 inch | 0.014 inch | 0.018 inch |
| Amount of paclitaxel | 3.2 µg/mm$^2$ | 3.6 µg/mm$^2$ | 3.6 µg/mm$^2$ | 3.2 µg/mm$^2$ | 3.2 µg/mm$^2$ |
| Diameter/length of core metal member | 0.39 mm/700 mm | 0.38 mm/500 mm | 0.38 mm/500 mm | 0.38 mm/700 mm | 0.48 mm/700 mm |
| Shape of core metal member | Wire-like | Wire-like | Wire-like | Wire-like | Wire-like |
| Material of core metal member | SUS | SUS | SUS | SUS | SUS |
| Material of holding portion | Silicone rubber | Silicone rubber | Silicone rubber | Silicone rubber | Silicone rubber |
| Shape/function of distal support of pleating section | Insertion into distal support | Insertion into distal support | Insertion into distal support | Insertion into distal support | Insertion into distal support |
| Number of blades in pleating section | Three | Three | Three | Three | Four |
| Characteristics of films | Difficult to electrostatically charge, smooth | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm | Teflon/0.001 mm |
| Control of pulling by collet chuck | — | — | — | — | — |
| Shape/function of distal support of folding section | Insertion into central portion of distal support | Insertion into central portion of distal support | Insertion into central portion of distal support | Insertion into central portion of distal support | Insertion into central portion of distal support |
| Number of blades in folding section | Ten | Ten | Ten | Ten | Ten |
| Control of pulling by collet chuck | — | — | — | — | — |
| Timing of start of rotation | Point of time when films contacted pleats | — | — | Point of time when films contacted pleats | — |
| Rotation of balloon catheter as viewed from proximal side | Counterclockwise | — | — | Counterclockwise | — |

TABLE 2

| Conditions | Example 6 | Example 7 | Example 8 | Example 9 |
|---|---|---|---|---|
| Diameter/length of balloon | 6.0 mm/200 mm | 4.0 mm/200 mm | 4.0 mm/200 mm | 4.0 mm/200 mm |
| Material of balloon | Nylon | Nylon | Nylon | Nylon |
| Surface condition of balloon catheter | Smooth, non-porous | Smooth, non-porous | Smooth, non-porous | Smooth, non-porous |
| Specification of guide wire lumen | 0.018 inch | 0.018 inch | 0.018 inch | 0.018 inch |
| Amount of paclitaxel | 3.2 µg/mm$^2$ | 3.2 µg/mm$^2$ | 3.2 µg/mm$^2$ | 3.2 µg/mm$^2$ |
| Diameter/length of core metal member | 0.48 mm/700 mm | 0.48 mm/700 mm | 0.48 mm/700 mm | 0.48 mm/700 mm |
| Shape of core metal member | Wire-like | Hollow | Hollow | Hollow |
| Material of core metal member | SUS | SUS | SUS | SUS |
| Material of holding portion | Silicone rubber | Silicone rubber | Silicone rubber | Silicone rubber |
| Shape/function of distal support of pleating section | Clamping in collet chuck | Clamping in collet chuck | Clamping in collet chuck | Clamping in collet chuck |
| Number of blades in pleating section | Four | Four | Four | Four |
| Characteristics of films | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |

TABLE 2-continued

| Conditions | Example 6 | Example 7 | Example 8 | Example 9 |
|---|---|---|---|---|
| Shape/function of distal support of folding section | Clamping in collet chuck | Clamping in collet chuck | Clamping in collet chuck | Clamping in collet chuck |
| Number of blades in folding section | Eight | Twelve | Twelve | Twelve |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Timing of start of rotation | Point of time when films contacted pleats | Point of time when films contacted pleats | Point of time when films contacted pleats | Point of time when films contacted pleats |
| Rotation of balloon catheter as viewed from proximal side | Counterclockwise | Counterclockwise | Counterclockwise | Counterclockwise |

TABLE 3

| Conditions | Example 10 | Example 11 | Example 12 | Example 13 |
|---|---|---|---|---|
| Diameter/length of balloon | 3.0 mm/20 mm | 4.0 mm/200 mm | 3.0 mm/200 mm | 2.0 mm/200 mm |
| Material of balloon | Nylon elastomer | Nylon | Nylon | Nylon |
| Surface condition of balloon catheter | Smooth, non-porous | Smooth, non-porous | Smooth, non-porous | Smooth, non-porous |
| Specification of guide wire lumen | 0.014 inch | 0.014 inch | 0.014 inch | 0.014 inch |
| Amount of paclitaxel | 3.2 µg/mm$^2$ | 3.6 µg/mm$^2$ | 3.6 µg/mm$^2$ | 3.2 µg/mm$^2$ |
| Diameter/length of core metal member | 0.38 mm/500 mm | 0.38 mm/500 mm | 0.38 mm/500 mm | 0.38 mm/700 mm |
| Shape of core metal member | Wire-like | Wire-like | Wire-like | Wire-like |
| Material of core metal member | SUS | SUS | SUS | SUS |
| Material of holding portion | Silicone rubber | Silicone rubber | Silicone rubber | Silicone rubber |
| Shape/function of distal support of pleating section | Insertion into distal support | Insertion into distal support | Insertion into distal support | Clamping in collet chuck |
| Number of blades in pleating section | Three | Three | Three | Four |
| Characteristics of films | Difficult to electrostatically charge, smooth | — | — | Difficult to electrostatically charge, smooth |
| Film (material/thickness) | Teflon/0.001 mm | None | None | Teflon/0.001 mm |
| Control of pulling by collet chuck | — | — | — | — |
| Shape/function of distal support of folding section | Insertion into distal support | Insertion into distal support | Insertion into distal support | Insertion into distal support |
| Number of blades in folding section | Twelve | Ten | Ten | Ten |
| Control of pulling by collet chuck | — | — | — | — |
| Timing of start of rotation | Point of time when films contacted pleats | — | — | — |
| Rotation of balloon catheter as viewed from proximal side | Counterclockwise | — | — | — |

TABLE 4

| Conditions | Example 14 | Example 15 | Example 16 | Example 17 | Comparative Example 1 |
|---|---|---|---|---|---|
| Diameter/length of balloon | 6.0 mm/80 mm | 6.0 mm/80 mm | 2.0 mm/200 mm | 7.0 mm/200 mm | 2.0 mm/200 mm |
| Material of balloon | Nylon | Nylon | Nylon | Nylon | Nylon |
| Surface condition of balloon catheter | Smooth, non-porous | Smooth, non-porous | Smooth, non-porous | Smooth, non-porous | Smooth, non-porous |
| Specification of guide wire lumen | 0.035 inch | 0.035 inch | 0.014 inch | 0.018 inch | 0.014 inch |
| Amount of paclitaxel | 3.2 µg/mm$^2$ | 3.6 µg/mm$^2$ | 3.6 µg/mm$^2$ | 3.2 µg/mm$^2$ | 3.2 µg/mm$^2$ |
| Diameter/length of core metal member | 0.91 mm/700 mm | 0.83 mm/700 mm | 0.30 mm/700 mm | 0.40 mm/700 mm | |
| Shape of core metal member | Wire-like | Wire-like | Wire-like | Wire-like | Wire-like |

TABLE 4-continued

| Conditions | Example 14 | Example 15 | Example 16 | Example 17 | Comparative Example 1 |
|---|---|---|---|---|---|
| Material of core metal member | SUS | SUS | SUS | SUS | SUS |
| Material of holding portion | Silicone rubber | Silicone rubber | Silicone rubber | Silicone rubber | Silicone rubber |
| Shape/function of distal support of pleating section | Insertion into distal support | Insertion into distal support | Insertion into distal support | Insertion into distal support | Insertion into distal support |
| Number of blades in pleating section | Four | Four | Three | Four | Three |
| Characteristics of films | Difficult to electrostatically charge, smooth | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm | Teflon/0.001 mm |
| Control of pulling by collet chuck | — | — | — | — | — |
| Shape/function of distal support of folding section | Insertion into center of distal support | Insertion into center of distal support | Insertion into center of distal support | Insertion into center of distal support | Insertion into center of distal support |
| Number of blades in folding section | Ten | Ten | Ten | Ten | Ten |
| Control of pulling by collet chuck | — | — | — | — | — |
| Timing of start of rotation | — | — | Point of time when films contacted pleats | — | Point of time when films contacted pleats |
| Rotation of balloon catheter as viewed from proximal side | — | — | Counterclockwise | — | Counterclockwise |

Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 2.0 mm in diameter and 40 mm in length when inflated, the balloon was inflated at 4 atm, and coating with the coating liquid was slowly conducted such that the amount of paclitaxel on the balloon would be approximately 3.2 μg/mm$^2$. After the coating, the balloon catheter was dried, to produce a drug-coated balloon.

(2) Step of Pleating the Drug-Coated Balloon

A core metal member (material: SUS) in the form of wire (solid) 0.39 mm in diameter and 700 mm in length was inserted into a guide wire lumen (0.014 inch specification: 0.40 to 0.44 mm) of the dried drug-coated balloon, the balloon catheter was placed on a support base of a balloon wrapping apparatus such that the drug coating portion did not make contact with the support base, and a shaft of the balloon catheter was fixed to a holding base section by a holding portion fitted with silicone rubber. Note that "a guide wire lumen (0.014 inch specification: 0.40 to 0.44 mm)" means a guide wire lumen for passing therethrough and using a guide wire having a diameter of 0.014 inch, the diameter (inside diameter) of the guide wire lumen being 0.40 to 0.44 mm (the same applies hereinafter). In this instance, the three-way stopcock of the hub of the balloon catheter was attached to an air injection and suction mechanism for inflating and deflating the balloon of the wrapping apparatus. The core metal member protruding from a distal portion of the balloon catheter was inserted into a distal support (assisting shaft) of a pleating section 2. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film were made contact with the pleats, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Example 2

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 4.0 mm in diameter and 200 mm in length when inflated, the balloon was inflated at 4 atm, and coating with the coating liquid was slowly conducted such that the amount of paclitaxel on the balloon would be approximately 3.6 μg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen (0.014 inch specification: 0.40 to 0.44 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 3

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 3.0 mm in diameter and 200 mm in length when inflated, the balloon was inflated at 4 atm, and coating with the coating liquid was slowly conducted such that the amount of paclitaxel on the balloon would be approximately 3.6 μg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen (0.014 inch specification: 0.40 to 0.44 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 4

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 μg/mm². After the coating, the balloon catheter was dried, to produce a drug-coated balloon.

(2) Step of Pleating the Drug-Coated Balloon

A core metal member (material: SUS) in the form of wire 0.38 mm in diameter and 700 mm in length was inserted into a guide wire lumen (0.014 inch specification: 0.40 to 0.44 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the pleats, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Example 5

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 6.0 mm in diameter and 200 mm in length when inflated, the balloon was inflated at 4 atm, and coating with the coating liquid was slowly conducted such that the amount of paclitaxel on the balloon would be approximately 3.2 μg/mm². After the coating, the balloon catheter was dried, to produce a drug-coated balloon.

(2) Step of Pleating the Drug-Coated Balloon

A core metal member (material: SUS) in the form of wire 0.48 mm in diameter and 700 mm in length was inserted into a guide wire lumen (0.018 inch specification: 0.50 to 0.54 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. Note that "a guide wire lumen (0.018 inch specification: 0.50 to 0.54 mm)" means a guide wire lumen for passing therethrough and using a guide wire having a diameter of 0.018 inch, the diameter (inside diameter) of the guide wire lumen being 0.50 to 0.54 mm (the same applies hereinafter). In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 6

(1) Production of Drug-Coated Balloon

In the same procedure as in the production example of the drug-coated balloon in Example 1, a drug-coated balloon of a balloon catheter (material of balloon: nylon, the surface being smooth and non-porous) 6.0 mm in diameter and 200 mm in length was produced.

(2) Step of Pleating the Drug-Coated Balloon

A core metal member (material: SUS) in the form of wire 0.48 mm in diameter and 700 mm in length was inserted into a guide wire lumen (0.018 inch specification: 0.50 to 0.54 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward by 5 mm and was fixed. The heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into, and fixed to, a collet chuck affixed to a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having eight blades. After the balloon was pushed in completely, the position of the distal support was fixed, and the support base section with the shaft of the balloon catheter fixed thereto was pulled backward by 5 mm and was fixed. The heated blades were slowly closed, then, from the point of time when the first film and the second film made contact with the pleats the balloon catheter was slowly rotated in the direction reverse to the rotary movement direction of the blades, and the rotation of the balloon was finished before the blades were closed completely. The eight blades were held in a closed state for a while, after which the blades were slowly opened, to spread the first film and the second film, and the balloon was drawn back from the folding section.

Example 7

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen (0.018 inch specification: 0.50 to 0.54 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward by 5 mm, and was then fixed. The heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward by 5 mm and was then fixed. The heated blades were slowly closed, then, from the point of time when the first film and the second film made contact with the pleats, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first films, and the balloon was drawn back from the folding section.

Example 8

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen (0.018 inch specification: 0.50 to 0.54 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward with a force of 5 N, and was then fixed. The heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the distal support was fixed, and the support base section with the shaft of the balloon catheter fixed thereto was pulled backward by a force of 5 N and was fixed. The heated blades were slowly closed, then, from the point of time when the first film and the second film made contact with the pleats, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 9

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen (0.018 inch specification: 0.50 to 0.54 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed, then, from the point of time when the first film and the second film made contact with the pleats, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 10

(1) Production of Drug-Coated Balloon

In the same procedure as in the production example of the drug-coated balloon in Example 1, a drug-coated balloon of a balloon catheter (material of balloon: nylon elastomer, the surface being smooth and non-porous) 3.0 mm in diameter and 20 mm in length was produced.

(2) Step of Pleating the Drug-Coated Balloon

A core metal member (material: SUS) in the form of wire 0.38 mm in diameter and 500 mm in length was inserted into a guide wire lumen (0.014 inch specification: 0.40 to 0.44 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft)

of the pleating section. Subsequently, the balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the heated blades were slowly closed, then, from the point of time when the first film and the second film made contact with the pleats, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first film and the second film. Thereafter, the balloon was drawn back from the folding section.

Example 11

(1) Production of Drug-Coated Balloon

In the same procedure as in the production example of the drug-coated balloon in Example 1, a drug coated balloon of a balloon catheter (material of balloon: nylon, the surface being smooth and non-porous) 4.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen (0.014 inch specification: 0.40 to 0.44 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Example 12

(1) Production of Drug-Coated Balloon

In the same procedure as in the production example of the drug-coated balloon in Example 1, a drug-coated balloon of a balloon catheter (material of balloon: nylon, the surface being smooth and non-porous) 3.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen (0.014 inch specification: 0.40 to 0.44 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Example 13

(1) Production of Drug-Coated Balloon

In the same procedure as in the production example of the drug-coated balloon in Example 1, a drug-coated balloon of a balloon catheter (material of balloon: nylon, the surface being smooth and non-porous) 2.0 mm in diameter and 200 mm in length was produced.

(2) Step of Pleating the Drug-Coated Balloon

A core metal member (material: SUS) in the form of wire 0.38 mm in diameter and 700 mm in length was inserted into a guide wire lumen (0.014 inch specification: 0.40 to 0.44 mm) of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into, and fixed to, a collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 14

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 6.0 mm in diameter and 80 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire 0.91 mm in diameter and 700 mm in length was inserted into a guide wire lumen (0.035 inch specification: 0.93 to 0.97 mm) of the dried drug-coated balloon, the balloon catheter was placed on a support base of a balloon wrapping apparatus such that the drug coating portion did not make contact with the support base, and a shaft of the balloon catheter was fixed to a holding base section by a holding portion fitted with silicone rubber. Note that "a guide wire lumen (0.035 inch specification: 0.93 to 0.97 mm)" means a guide wire lumen for passing therethrough and using a guide wire having a diameter of 0.035 inch, the diameter (inside diameter) of the guide wire lumen being 0.93 to 0.97 mm (the same applies hereinafter). In this instance, the three-way stopcock of the hub of the balloon catheter was attached to an air injection and suction mechanism for inflating and deflating the balloon of the wrapping apparatus. The core metal member protruding from a distal portion of the balloon catheter was inserted into a distal support (assisting shaft) of a pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 15

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 6.0 mm in diameter and 80 mm in length when inflated, the balloon was inflated at 4 atm, and coating with the coating liquid was slowly conducted such that the amount of paclitaxel on the balloon would be approximately 3.2 μg/mm². After the coating, the balloon catheter was dried, to produce a drug-coated balloon.

(2) Step of Pleating the Drug-Coated Balloon

A core metal member (material: SUS) in the form of wire 0.83 mm in diameter and 700 mm in length was inserted into a guide wire lumen (0.035 inch specification: 0.93 to 0.97 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 16

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 μg/mm². After the coating, the balloon catheter was dried, to produce a drug-coated balloon.

(2) Step of Pleating the Drug-Coated Balloon

A core metal member (material: SUS) in the form of wire 0.30 mm in diameter and 700 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 17

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 7.0 mm in diameter and 200 mm in length when inflated, the balloon was inflated at 4 atm, and coating with the coating liquid was slowly conducted such that the amount of paclitaxel on the balloon would be approximately 3.2 μg/mm². After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen (0.018 inch specification: 0.50 to 0.54 mm) of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Comparative Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way stopcock was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 µg/mm². After the coating, the balloon catheter was dried, to produce a drug-coated balloon.

(2) Step of Pleating the Drug-Coated Balloon

The dried drug-coated balloon was placed on a support base of a balloon wrapping apparatus such that the drug coating portion did not make contact with the support base, and a shaft of the balloon catheter was fixed to the holding base section by the holding portion fitted with silicone rubber. In this instance, the three-way stopcock of the hub of the balloon catheter was attached to the air injection and suction mechanism for inflating and deflating the balloon of the wrapping apparatus. A distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form pleats, and then the blades were slowly opened, to spread the films. Thereafter, the balloon was drawn back from the pleating section.

(3) Step of Folding the Drug-Coated Balloon

In a condition where the balloon catheter formed with the pleats was held in a deflated state, the support base was slid or moved to the folding section. Next, the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

[Measurement of Amount of Paclitaxel Remaining on Balloon after Folding]

For the drug-coated balloons produced in Examples 1 to 5 and Examples 11 to 17, the amount of paclitaxel remaining on the balloon was measured in the following procedure.

(1) Method

The drug-coated balloon after folding was immersed in a methanol solution, followed by shaking by use of a shaker for 10 minutes, to extract paclitaxel present in the coating on the balloon. The light absorbance, at 227 nm, of the methanol solution into which paclitaxel had been extracted was measured by high-speed liquid chromatography using an ultraviolet-and-visible absorptiometer, and the amount of paclitaxel per balloon ([µg/balloon]) was determined. Further, from the amount of paclitaxel thus obtained and the surface area of the balloon, the amount of paclitaxel per unit area of balloon ([µg/mm²]) was calculated.

(2) Results

In Table 5, the amount of paclitaxel (theoretical value) on the balloon upon coating and the amount of paclitaxel (measured value) on the balloon after folding are depicted as amount per unit area. In addition, retention rate of paclitaxel after folding was calculated by dividing the amount of paclitaxel on the balloon after folding by the amount of paclitaxel on the balloon upon coating, and multiplying the quotient by 100.

As depicted in Table 5, in every one of Examples 1 to 5, and 14 to 17 the retention rate of paclitaxel was high. On the other hand, in Examples 11, 12 and 14 to 17, the retention rate of paclitaxel was as low as less than 80%. The films were used in the pleating and folding in Examples 1 to 5, but films were not used in the pleating and folding in Examples 11 and 12. It could be confirmed that detachment of the drug coating layer can be reduced by using films in pleating and folding.

TABLE 5

| Examples | Presence/absence of films | Size (diameter/length) of balloon | Amount of paclitaxel per unit area [μg/mm²] After Coating | Amount of paclitaxel per unit area [μg/mm²] After folding | Retention rate of paclitaxel (%) |
|---|---|---|---|---|---|
| Example 1 | Present | 2.0 mm/40 mm | 3.2 | 2.8 | 88 |
| Example 2 | Present | 4.0 mm/200 mm | 3.6 | 3.5 | 97 |
| Example 3 | Present | 3.0 mm/200 mm | 3.6 | 3.3 | 92 |
| Example 4 | Present | 2.0 mm/200 mm | 3.2 | 3.1 | 96 |
| Example 5 | Present | 6.0 mm/200 mm | 3.2 | 3.1 | 97 |
| Example 11 | Absent | 4.0 mm/200 mm | 3.6 | 2.8 | 78 |
| Example 12 | Absent | 3.0 mm/200 mm | 3.6 | 2.6 | 72 |
| Example 14 | Present | 6.0 mm/80 mm | 3.2 | 3.1 | 97 |
| Example 15 | Present | 6.0 mm/80 mm | 3.2 | 3.0 | 93 |
| Example 16 | Present | 2.0 mm/200 mm | 3.2 | 2.9 | 89 |
| Example 17 | Present | 7.0 mm/200 mm | 3.2 | 3.0 | 94 |

[Evaluation of Generation of Back Folding and Defective Pleats Upon Folding]

For the drug-coated balloons prepared under the conditions of Example 4 and Example 13, the generation rate of back folding upon folding was evaluated.

(1) Method

The wrapping direction of pleats of the drug-coated balloons upon folding was observed on a digital microscope. In the case where the wrapping directions of the pleats were not in one direction and there was the pleats whose wrapping direction was reverse to the normal direction, the case was counted as back folding. In addition, of the pleats formed, those of which the pleat size was not uniform upon visual inspection were classified as defective pleats.

(2) Results of Evaluation of Generation of Back Folding

Table 6 depicts the number of drug-coated balloons in which back folding was generated, the total number of drug-coated balloons subjected to folding, and generation rate of back folding. The generation rate of back folding was calculated by dividing the number of drug-coated balloons in which back folding was generated by the total number of drug-coated balloons subjected to folding, and multiplying the quotient by 100.

As depicted in Table 6, in the method of Example 4 in which the balloon was rotated during folding, back folding was scarcely generated. On the other hand, in the method of Example 13 in which the balloon was not rotated during folding, back folding was generated in approximately one half of the samples subjected to folding. Accordingly, it could be confirmed that the rotation of the balloon during folding has an effect to reduce the generation of back folding.

TABLE 6

| Examples | Rotation of balloon during folding | Number of drug-coated balloons in which back folding was generated [(Number of drug-coated balloons in which back folding was generated)/(Total number of drug-coated balloons subjected to folding)] | Generation rate of back folding [%] |
|---|---|---|---|
| Example 4 | Performed | 1/142 | 0.7 |
| Example 13 | Not performed | 22/46 | 48 |

(3) Results of Evaluation of Generation of Defective Pleats

Table 7 depicts the number of defective pleats generated, the total number of pleats formed, and a value obtained by dividing the number of defective pleats generated by the total number of pleats formed and multiplying the quotient by 100.

As depicted in Table 7, according to the method of Example 4 in which the core metal was inserted at the time of pleating, few defective pleats were generated. On the other hand, according to the method of Comparative Example 1 in which the core metal was not inserted at the time of pleating, many defective pleats were generated. It was confirmed that insertion of the core metal at the time of pleating has an effect to reduce the generation of defective pleats.

TABLE 7

| Examples | Presence or absence of core metal at the time of pleating | Number of defective pleats Generated [(number generated)/(total number of pleats formed)] | Generation rate of defective pleats [%] |
|---|---|---|---|
| Example 4 | Present | 1/142 | 0.7 |
| Comparative Example 1 | Absent | 4/5 | 80 |

The detailed description above describes embodiments of a balloon wrapping apparatus and a balloon wrapping method representing examples of the inventive balloon wrapping apparatus and a balloon wrapping method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon wrapping apparatus for wrapping a balloon provided at a distal portion of an elongated shaft of a balloon catheter, the balloon wrapping apparatus comprising:
    a pleating section configured to form the balloon with a plurality of circumferentially spaced apart pleats;
    a folding section that folds the plurality of pleats formed in the balloon, along a circumferential direction;
    a support base that supports the shaft of the balloon catheter, the support base being movable toward and away from one of the pleating section and the folding section, the movement of the support base toward the one of the pleating section and the folding section while the support base supports the shaft of the balloon catheter resulting in the balloon at the distal portion of the shaft of the balloon catheter being positioned for insertion into the one of the pleating section and the folding section;
    the one of the pleating section and the folding section including one side and an other side opposite the one side, the one side being provided with an insertion hole through which the balloon is insertable during the movement of the support base toward the one of the pleating section and the folding section, the other side being provided with a back surface hole that communicates with the insertion hole;
    the one of the pleating section and the folding section including an assisting shaft positioned to be inserted into the back surface hole from a back surface side of the other side, the one of the pleating section and the folding section also including an interlock portion configured to interlock with a part of the assisting shaft that is not inserted into the back surface hole while the assisting shaft is inserted into the back surface hole; and the assisting shaft including a cavity portion from a side facing to the back surface hole.

2. The balloon wrapping apparatus according to claim 1, further comprising a core metal member configured to be positioned in the shaft of the balloon catheter before the shaft of the balloon catheter is inserted into the one of the pleating section and the folding section, the core metal member being configured to be inserted into the cavity portion of the assisting shaft.

3. The balloon wrapping apparatus according to claim 2, wherein
the one of the pleating section and the folding section includes a plurality of blades aligned in a circumferential direction for shaping the balloon, and
the core metal member possesses a length greater than a length of the plurality of blades in the extending direction by not less than 10 mm.

4. The balloon wrapping apparatus according to claim 1, wherein the one of the pleating section and the folding section includes a plurality of blades aligned in a circumferential direction for shaping the balloon, and the assisting shaft including a decreasing diameter portion in which an outside diameter of the assisting shaft decreases toward the back surface hole before the assisting shaft is inserted into the back surface hole; and
the balloon wrapping apparatus further comprising two films passing through a central portion of the one of the pleating section and the folding section, the two films being surrounded by the plurality of blades.

5. The balloon wrapping apparatus according to claim 4, wherein
the plurality of blades extend in an extending direction from the insertion hole toward the back surface hole, and
the assisting shaft being moved together with the support base in a movement direction that is parallel to the extending direction of the blades.

6. The balloon wrapping apparatus according to claim 1, wherein the assisting shaft includes an elongated shaft main body and an inner surface member disposed on the shaft main body, the cavity portion being provided in the inner surface member, and the inner surface member being formed of a material higher in frictional coefficient than the shaft main body.

7. The balloon wrapping apparatus according to claim 1, wherein the assisting shaft includes an elongated shaft main body and an inner surface member disposed on the shaft main body, the cavity portion being provided in the inner surface member, and the inner surface member being formed of an elastic material.

8. The balloon wrapping apparatus according to claim 1, wherein the cavity portion extends into the assisting shaft in a depth direction from a free end of the assisting shaft, the cavity portion possessing an inside diameter that decreases toward the depth direction.

9. The balloon wrapping apparatus according to claim 1, wherein a maximum outer diameter of the assisting shaft is greater than an outer diameter of the balloon as the balloon is being inserted through the insertion hole.

10. The balloon wrapping apparatus according to claim 1, wherein the one of the pleating section and the folding section is the pleating section, and wherein the folding section includes one side and an other side opposite the one side of the folding section, the one side of the folding section being provided with an insertion hole, the other side of the folding section being provided with a back surface hole that communicates with the insertion hole of the folding section.

11. The balloon wrapping apparatus according to claim 1, wherein the one of the pleating section and the folding section is the folding section, and wherein the pleating section includes one side and an other side opposite the one side of the pleating section, the one side of the pleating section being provided with an insertion hole, the other side of the pleating section being provided with a back surface hole that communicates with the insertion hole of the pleating section.

12. A balloon wrapping apparatus for wrapping a balloon at a distal portion of an elongated shaft of a balloon catheter, the distal portion of the elongated shaft terminating in a free end, the balloon wrapping apparatus comprising:
a pleating section comprised of first and second walls spaced apart from one another so that a space exists in the pleating section between the first and second walls into which the balloon at the distal portion of the elongated shaft of the balloon catheter is movable, the space in the pleating section containing a first plurality of rotatable blades that engage the balloon when the balloon is positioned in the space to form a plurality of circumferentially spaced apart pleats on the balloon;
a folding section comprised of first and second walls spaced apart from one another so that a space exists between the first and second walls of the folding section into which the balloon at the distal portion of the elongated shaft of the balloon catheter is movable, the space in the folding section containing a second plurality of rotatable blades that engage the balloon when the balloon is positioned in the space in the folding section to fold the pleats along a circumferential direction;
the first and second walls of one of the pleating section and the folding section including a first through hole and a second through hole respectively, the first and second through holes being aligned with one another;
a support base configured to support the shaft of the balloon catheter, the support base being movable in a first direction toward the first wall that includes the first through hole so that the balloon on the distal portion of the shaft approaches the first through hole; and
the one of the pleating section and the folding section including an elongated assisting shaft projecting toward the second wall that includes the second through hole, the assisting shaft being movable in a second direction, opposite the first direction, toward the second wall that includes the second through hole to cause the assisting shaft to pass through the second through hole and to interact with the shaft of the balloon catheter supported on the support base so that the assisting shaft supports the free end of the shaft to prevent the shaft from bending due to gravity.

13. The balloon wrapping apparatus according to claim 12, wherein the assisting shaft possesses a central axis that passes through both the first and second through openings.

14. The balloon wrapping apparatus according to claim 12, further comprising an interlock shaft fixed to and movable with the assisting shaft, and an interlock portion fixed to and movable with the support base, the interlock shaft being configured to engage the interlock portion as the assisting shaft moves in the first direction.

15. The balloon wrapping apparatus according to claim 12, further comprising a core metal member configured to be positioned in the shaft of the balloon catheter, the assisting shaft being configured to engage the core metal member after the assisting shaft moves in the second direction to effect the support of the free end of the shaft and prevent the shaft from bending due to gravity.

16. The balloon wrapping apparatus according to claim 12, wherein the assisting shaft includes a distal free end portion provided with an axially extending cavity configured to receive a core metal member positioned inside the shaft of the balloon catheter.

17. The balloon wrapping apparatus according to claim 12, wherein the plurality of blades in the one of the pleating section and the folding section extend in an extending direction from the first through hole toward the second through hole, and the second direction being parallel to the extending direction of the blades in the one of the pleating section and the folding section.

18. The balloon wrapping apparatus according to claim 12, wherein the first and second walls of the pleating section include the first through hole and the second through hole respectively, and wherein the first and second walls of the folding section include a first through hole and a second through hole respectively that are aligned with one another.

19. The balloon wrapping apparatus according to claim 12, wherein the first and second walls of the folding section include the first through hole and the second through hole respectively, and wherein the first and second walls of the pleating section include a first through hole and a second through hole respectively that are aligned with one another.

* * * * *